US007294152B2

(12) United States Patent
Lagrange

(10) Patent No.: US 7,294,152 B2
(45) Date of Patent: Nov. 13, 2007

(54) DYEING COMPOSITION COMPRISING AT LEAST ONE FLUORINDINE COMPOUND FOR THE DYEING OF KERATINIC FIBERS, DYEING PROCESS COMPRISING THE COMPOSITION AND COMPOUND

(75) Inventor: Alain Lagrange, Coupvray (FR)

(73) Assignee: L'Oreal S.A., Paris (FR)

( * ) Notice: Subject to any disclaimer, the term of this patent is extended or adjusted under 35 U.S.C. 154(b) by 305 days.

(21) Appl. No.: 11/030,170

(22) Filed: Jan. 7, 2005

(65) Prior Publication Data
US 2005/0188475 A1 Sep. 1, 2005

Related U.S. Application Data

(60) Provisional application No. 60/549,534, filed on Mar. 4, 2004.

(51) Int. Cl.
A61K 7/13 (2006.01)
(52) U.S. Cl. ........................ 8/405; 8/426; 8/454; 8/462; 8/552; 8/554; 8/565; 8/657; 544/340
(58) Field of Classification Search ............... 8/405, 8/426, 454, 462, 552, 554, 565, 657; 544/340
See application file for complete search history.

(56) References Cited

U.S. PATENT DOCUMENTS

| 2,047,398 A | 7/1936 | Voss et al. |
| 2,261,002 A | 10/1941 | Ritter |
| 2,271,378 A | 1/1942 | Searle et al. |
| 2,273,780 A | 2/1942 | Dittmar |
| 2,375,853 A | 5/1945 | Kirby et al. |
| 2,388,614 A | 11/1945 | Kirby et al. |
| 2,454,547 A | 11/1948 | Bock et al. |
| 2,528,378 A | 10/1950 | Mannheimer |
| 2,781,354 A | 2/1957 | Mannheimer |
| 2,798,053 A | 7/1957 | Brown |
| 2,923,692 A | 2/1960 | Ackerman et al. |
| 2,961,347 A | 11/1960 | Floyd |
| 3,206,462 A | 9/1965 | McCarty |
| 3,227,615 A | 1/1966 | Korden |
| 3,390,948 A * | 7/1968 | Straley et al. .................. 8/657 |
| 3,472,840 A | 10/1969 | Stone et al. |
| 3,632,559 A | 1/1972 | Matter et al. |
| 3,770,683 A | 11/1973 | Barabas et al. |
| 3,810,977 A | 5/1974 | Levine et al. |
| 3,836,537 A | 9/1974 | Boerwinkle et al. |
| 3,874,870 A | 4/1975 | Green et al. |
| 3,910,862 A | 10/1975 | Barabas et al. |
| 3,912,808 A | 10/1975 | Sokol |
| 3,915,921 A | 10/1975 | Schlatzer, Jr. |
| 3,917,817 A | 11/1975 | Vanlerberghe et al. |
| 3,925,542 A | 12/1975 | Viout et al. |
| 3,929,735 A | 12/1975 | Barabas |
| 3,929,990 A | 12/1975 | Green et al. |
| 3,946,749 A | 3/1976 | Papantoniou |
| 3,966,403 A | 6/1976 | Papantoniou |
| 3,966,404 A | 6/1976 | Papantoniou et al. |
| 3,966,904 A | 6/1976 | Green et al. |
| 3,986,825 A | 10/1976 | Sokol |
| 3,990,459 A | 11/1976 | Papantoniou |
| 4,001,432 A | 1/1977 | Green et al. |
| 4,005,193 A | 1/1977 | Green et al. |
| 4,013,787 A | 3/1977 | Varlerberghe et al. |
| 4,025,617 A | 5/1977 | Green et al. |
| 4,025,627 A | 5/1977 | Green et al. |
| 4,025,653 A | 5/1977 | Green et al. |
| 4,026,945 A | 5/1977 | Green et al. |
| 4,027,020 A | 5/1977 | Green et al. |
| 4,031,307 A | 6/1977 | DeMartino et al. |
| 4,070,533 A | 1/1978 | Papantoniou et al. |
| 4,075,136 A | 2/1978 | Schaper |
| 4,076,912 A | 2/1978 | Papantoniou et al. |
| 4,128,631 A | 12/1978 | Lundmark et al. |
| 4,129,711 A | 12/1978 | Viout et al. |
| 4,131,576 A | 12/1978 | Iovine et al. |
| 4,137,208 A | 1/1979 | Elliott |
| 4,165,367 A | 8/1979 | Chakrabarti |
| 4,166,894 A | 9/1979 | Schaper |
| 4,189,468 A | 2/1980 | Vanlerberghe et al. |
| 4,223,009 A | 9/1980 | Chakrabarti |
| 4,237,243 A | 12/1980 | Quack et al. |
| 4,277,581 A | 7/1981 | Vanlerberghe et al. |
| 4,278,571 A | 7/1981 | Choy |
| 4,282,203 A | 8/1981 | Jacquet et al. |
| 4,289,752 A | 9/1981 | Mahieu et al. |
| 4,349,532 A | 9/1982 | Vanlerberghe et al. |
| 4,509,949 A | 4/1985 | Huang et al. |
| 4,591,610 A | 5/1986 | Grollier |
| 4,608,250 A | 8/1986 | Jacquet et al. |
| 4,677,155 A | 6/1987 | Finter |
| 4,693,935 A | 9/1987 | Mazurek |
| 4,719,099 A | 1/1988 | Grollier et al. |
| 4,761,273 A | 8/1988 | Grollier et al. |
| 4,797,347 A | 1/1989 | Finter |
| 4,839,166 A | 6/1989 | Grollier et al. |
| 4,957,732 A | 9/1990 | Grollier et al. |

(Continued)

FOREIGN PATENT DOCUMENTS

DE 2 330 956 1/1974

(Continued)

OTHER PUBLICATIONS

STIC Search Report dated Nov. 27, 2006.*

(Continued)

Primary Examiner—Eisa Elhilo
(74) Attorney, Agent, or Firm—Finnegan, Henderson, Farabow, Garrett, & Dunner, LLP

(57) ABSTRACT

The present disclosure relates to a specific direct dye compound that is a fluorindine derivative, and dyeing compositions comprising at least one derivative of the compound and at least one polymer. A process for dyeing keratin fibers with the defined compositions is also disclosed.

25 Claims, No Drawings

U.S. PATENT DOCUMENTS

| | | | |
|---|---|---|---|
| 4,972,037 | A | 11/1990 | Garbe et al. |
| 4,996,059 | A | 2/1991 | Grollier et al. |
| 5,009,880 | A | 4/1991 | Grollier et al. |
| 5,089,252 | A | 2/1992 | Grollier et al. |
| 5,139,037 | A | 8/1992 | Grollier et al. |
| 5,158,762 | A | 10/1992 | Pierce |
| 5,196,189 | A | 3/1993 | Jacquet et al. |
| 5,506,315 | A | 4/1996 | Meyer et al. |
| 5,958,392 | A | 9/1999 | Grollier et al. |
| 6,120,780 | A | 9/2000 | Dupuis et al. |
| 7,066,966 | B2 | 6/2006 | Cottard et al. |
| 2003/0124079 | A1 | 7/2003 | Mougin et al. |
| 2004/0141943 | A1 | 7/2004 | Mougin et al. |

FOREIGN PATENT DOCUMENTS

| | | |
|---|---|---|
| DE | 39 27 480 | 2/1991 |
| EP | 0 080 975 | 6/1983 |
| EP | 0 090 493 | 10/1983 |
| EP | 0 122 324 | 10/1984 |
| EP | 0 173 109 | 3/1986 |
| EP | 0 186 507 | 7/1986 |
| EP | 0 337 354 | 10/1989 |
| EP | 0 395 282 | 10/1990 |
| EP | 0 412 704 | 2/1991 |
| EP | 0 412 707 | 2/1991 |
| EP | 0 448 978 | 10/1991 |
| EP | 0 503 853 | 9/1992 |
| EP | 0 582 152 | 2/1994 |
| EP | 0 815 828 | 1/1998 |
| FR | 1 222 944 | 6/1960 |
| FR | 1 492 597 | 8/1967 |
| FR | 1 564 110 | 4/1969 |
| FR | 1 580 545 | 9/1969 |
| FR | 1 583 363 | 10/1969 |
| FR | 2 077 143 | 10/1971 |
| FR | 2 080 759 | 11/1971 |
| FR | 2 102 113 | 4/1972 |
| FR | 2 162 025 | 7/1973 |
| FR | 2 190 406 | 2/1974 |
| FR | 2 252 840 | 6/1975 |
| FR | 2 265 781 | 10/1975 |
| FR | 2 265 782 | 10/1975 |
| FR | 2 270 846 | 12/1975 |
| FR | 2 280 361 | 2/1976 |
| FR | 2 316 271 | 1/1977 |
| FR | 2 320 330 | 3/1977 |
| FR | 2 336 434 | 7/1977 |
| FR | 2 350 384 | 12/1977 |
| FR | 2 357 241 | 2/1978 |
| FR | 2 368 508 | 5/1978 |
| FR | 2 383 660 | 10/1978 |
| FR | 2 393 573 | 1/1979 |
| FR | 2 413 907 | 8/1979 |
| FR | 2 416 723 | 9/1979 |
| FR | 2 439 798 | 5/1980 |
| FR | 2 470 596 | 6/1981 |
| FR | 2 505 348 | 11/1982 |
| FR | 2 519 863 | 7/1983 |
| FR | 2 542 997 | 9/1984 |
| FR | 2 589 476 | 5/1987 |
| FR | 2 598 611 | 11/1987 |
| FR | 2 811 993 | 1/2002 |
| FR | 2 820 032 | 8/2002 |
| GB | 839 805 | 6/1960 |
| GB | 922 457 | 4/1963 |
| GB | 1 334 416 | 10/1973 |
| GB | 1 546 809 | 5/1979 |
| GB | 1 572 626 | 7/1980 |
| LU | 75370 | 2/1978 |
| LU | 75371 | 2/1978 |
| WO | WO 93/23009 | 11/1993 |
| WO | WO 93/23446 | 11/1993 |
| WO | WO 95/00578 | 1/1995 |
| WO | WO 96/06592 | 3/1996 |
| WO | WO 96/10593 | 4/1996 |
| WO | WO 99/07757 | 2/1999 |
| WO | WO 00/68282 | 11/2000 |

OTHER PUBLICATIONS

Fonnum et al. "Associative Thickeners, Part I: Synthesis, rheology and aggregration behavior;"Colloid Polym. Sci 271: 380-389 (1993).

English Language Derwent Abstract to DE 39 27 480, (Feb. 21, 1991).

English Language Derwent Abstract to FR 2 357 241, (Feb. 3, 1978).

English Language Derwent Abstract for FR 2 589 476, (May 7, 1987).

French Search Report for FR 04 50041 (French Priority Application for the present application) Dec. 15, 2003.

* cited by examiner

DYEING COMPOSITION COMPRISING AT LEAST ONE FLUORINDINE COMPOUND FOR THE DYEING OF KERATINIC FIBERS, DYEING PROCESS COMPRISING THE COMPOSITION AND COMPOUND

This application claims benefit of U.S. Provisional Application No. 60/549,534, filed Mar. 4, 2004.

The present disclosure relates to, as a direct dye, at least one compound of the fluorindine type for the dyeing of keratinic fibers, such as human, fibers, and a dyeing composition comprising the compound. The present disclosure additionally concerns a process for dyeing keratin fibers using compositions as such.

There are essentially two methods for dyeing keratinic, such as human, fibers, and for instance, the hair.

The first method, also called permanent dyeing, comprises the application of at least one precursor of an oxidation dye (or oxidation base) to the fibers, optionally in combination with at least one coupler which makes it possible to vary the shade obtained with the precursor or precursors, in the presence of an oxidizing agent. The oxidation dyes and couplers are colorless or weakly colored compounds which, in combination with oxidizing substances, can lead to colored compounds by a process of oxidative condensation.

Due to the multiple combinations possible between the different oxidation bases and couplers, permanent dyeing makes it possible to obtain a large range of colors. These compounds can, in certain cases, give rise to safety problems. Further, they may result in colorations whose fastness (i.e. longevity) is difficult to control, which can lead to undesired, selective shifts in the color. Finally, the presence of an oxidising agent can lead to degradation of the keratinic fiber.

The second method, also called semi-permanent dyeing, consists in the use of at least one direct dye, which is a colored compound which dyes keratinic fibers. Such compounds can, if necessary or desired, be applied to the fibers in the presence of at least one oxidizing agent. Such an instance is referred to as lightening direct dyeing.

One disadvantage of direct dyeing can be its lack of fastness, such as towards shampoos. Further, with this type of dyeing it can be difficult to obtain natural or grey shades of good quality.

Accordingly, the present disclosure relates to a dyeing composition for the dyeing of keratinic fibers, such as human fibers, comprising as a direct dye, in a medium appropriate for the dyeing of the fibers, at least one compound of formula (I):

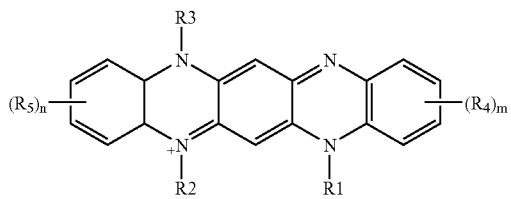

wherein:

$R_1$, $R_2$ and $R_3$, which may be the same or different, are chosen from linear and branched $C_1$-$C_{24}$ alkyl groups, $C_6$-$C_{30}$ aryl groups, and aralkyl groups, wherein the aryl part is $C_6$-$C_{30}$ and the linear or branched alkyl part is $C_1$-$C_{24}$;

$R_4$ and $R_5$, which may be the same or different, are chosen from hydrogen atoms, halogen atoms, hydroxy groups, linear and branched $C_1$-$C_{24}$ alkyl groups, linear and branched $C_1$-$C_{24}$ alkoxy groups, monohydroxy alkoxy groups wherein the alkyl part is linear or branched $C_1$-$C_6$, polyhydroxy alkoxy groups wherein the alkyl part is linear or branched $C_1$-$C_6$, amino groups optionally substituted with at least one group chosen from linear and branched $C_1$-$C_6$ alkyl groups, which may be the same or different, optionally substituted with at least one hydroxyl group, thiol groups, alkylthio groups, wherein the alkyl part is linear or branched $C_1$-$C_6$, carboxyl groups in acid or salt form (with an alkali metal or substituted or unsubstituted ammonium), alkoxycarbonyl groups wherein the alkyl part is linear or branched $C_1$-$C_6$, alkylamide groups wherein the alkyl part is linear or branched $C_1$-$C_6$, alkylcarbamyl groups wherein the alkyl part is linear or branched $C_1$-$C_6$, cyano groups, nitro groups, sulphonyl groups, alkylsulphonyl groups wherein the alkyl part is linear or branched $C_1$-$C_6$, alkylsulphonylamido groups wherein the alkyl part is linear or branched $C_1$-$C_6$, $C_6$-$C_{30}$ aryl groups optionally substituted with at least one $C_1$-$C_6$ alkyl group, and aralkyl groups wherein the aryl part is $C_6$-$C_{30}$, optionally substituted with at least one $C_1$-$C_6$ alkyl group, and the linear or branched alkyl part is $C_1$-$C_{24}$, wherein the alkyl and aryl groups and/or parts are optionally substituted with at least one entity chosen from hydroxyl groups, —$SO_3^-$ groups, —$COO^-$ groups, halogen atoms, $C_1$-$C_6$ alkoxy groups, monohydroxy alkoxy groups wherein the alkyl part is linear or branched $C_1$-$C_6$, polyhydroxy alkoxy groups wherein the alkyl part is linear or branched $C_1$-$C_6$, amino groups optionally substituted with at least one group chosen from linear and branched $C_1$-$C_6$ alkyl groups which may be the same or different, optionally substituted with at least one hydroxyl group, n and m, which may be the same or different, are integers from 0 to 4,- An is at least one anion chosen from cosmetically acceptable anions; and p is equal to 0 or 1, so as to respect the electroneutrality of the compound.

A further aspect of the present disclosure is a dyeing composition comprising as a direct dye, in a medium appropriate for the dyeing, at least one compound of the previously described formula (I) and at least one additive selected from surfactants and polymers.

Still another aspect of the present disclosure is a process for the dyeing of keratinic, such as human, materials, involving the compounds of formula (I).

Yet still another aspect of the present disclosure are the compounds of formula (I) themselves.

It has been found, surprisingly, that the use of such a dyeing composition made it possible to obtain intense colorations, even on non-sensitized hair. For example, outstanding blues may be obtained.

Moreover, the compounds of formula (I), in addition to being safe, can make it possible to obtain blue highlights, which can be at least one of chromatic or dark, very powerful, of low selectivity, and fast to the various influences to which hair can be subjected, such as for instance, shampoos, permanent waves, the action of light, and perspiration.

Other characteristics and benefits of the present disclosure will appear more clearly from the reading of the description that is to follow.

As was stated above, the present disclosure relates to the use of a dyeing composition comprising, as a direct dye, in an appropriate medium, at least one compound of formula (I):

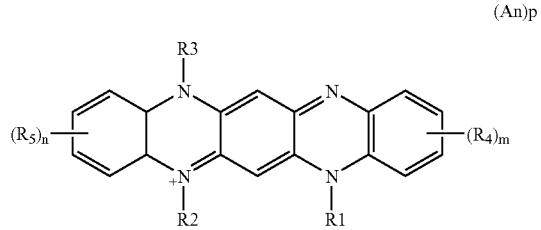

wherein:

$R_1$, $R_2$ and $R_3$, which may be the same or different, are chosen from linear and branched $C_1$-$C_{24}$ alkyl groups, $C_6$-$C_{30}$ aryl groups, and aralkyl groups wherein the aryl part is $C_6$-$C_{30}$ and the linear or branched alkyl part is $C_1$-$C_{24}$;

$R_4$ and $R_5$, which may be the same or different, are chosen from hydrogen atoms, halogen atoms, hydroxy groups, linear and branched $C_1$-$C_{24}$ alkyl groups, linear and branched $C_1$-$C_{24}$ alkoxy groups, monohydroxy alkoxy group wherein the alkyl part is linear or branched $C_1$-$C_6$, polyhydroxy alkoxy groups wherein the alkyl part is linear or branched $C_1$-$C_6$, amino groups optionally substituted with at least one group chosen from linear and branched $C_1$-$C_6$ alkyl groups which may be the same or different, optionally substituted with at least one hydroxyl group, thiol groups, alkylthio groups wherein the alkyl part is linear or branched $C_1$-$C_6$, carboxyl groups in acid or salt form (with an alkali metal or substituted or unsubstituted ammonium), alkoxycarbonyl group wherein the alkyl part is linear or branched $C_1$-$C_6$, alkylamide groups wherein the alkyl part is linear or branched $C_1$-$C_6$, alkylcarbamyl groups wherein the alkyl part is linear or branched $C_1$-$C_6$, cyano groups, nitro groups, sulphonyl groups, alkylsulphonyl groups wherein the alkyl part is linear or branched $C_1$-$C_6$, alkylsulphonylamido groups wherein the alkyl part is linear or branched $C_1$-$C_6$, $C_6$-$C_{30}$ aryl groups optionally substituted with at least one $C_1$-$C_6$ alkyl group, and aralkyl groups wherein the aryl part is $C_6$-$C_{30}$, optionally substituted with at least one $C_1$-$C_6$ alkyl group, and the linear or branched alkyl part is $C_1$-$C_{24}$, wherein the alkyl and aryl groups and/or parts are optionally substituted with at least one entity chosen from hydroxyl groups, —$SO_3^-$ groups, —$COO^-$ groups, halogen atoms, $C_1$-$C_6$ alkoxy groups, monohydroxy alkoxy groups wherein the alkyl part is linear or branched $C_1$-$C_6$, polyhydroxy alkoxy groups wherein the alkyl part is linear or branched $C_1$-$C_6$, and amino groups optionally substituted with at least one group chosen from linear and branched $C_1$-$C_6$ alkyl groups which may be the same or different, optionally substituted with at least one hydroxyl group, n and m, which may be the same or different, are integers from 0 to 4, An is at least one anion chosen from cosmetically acceptable anions; and p is equal to 0 or 1, so as to respect the electroneutrality of the compound.

According to one aspect of the present disclosure, in the formula (I) the groups $R_1$, $R_2$ and $R_3$, which may be the same or different, may be chosen from $C_1$-$C_6$ alkyl groups, phenyl groups, and aralkyl groups, wherein the aryl part is $C_6$ and the alkyl part is $C_1$-$C_6$, wherein the alkyl, phenyl and aralkyl groups are optionally substituted with at least one entity chosen from hydroxyl groups, —$SO_3^-$ groups, —$COO^-$ groups, halogen atoms, $C_1$-$C_6$ alkoxy groups, amino groups, (di)alkylamino groups wherein the alkyl part is $C_1$-$C_6$, and (di)hydroxyalkylamino groups wherein the alkyl part is $C_1$-$C_6$. For example, the groups $R_1$, $R_2$ and $R_3$, which may be the same or different, may be chosen from methyl, ethyl, methoxy, hydroxyethyl, phenyl and 3-sulphopropyl groups.

According to another aspect of the present disclosure, $R_4$ and $R_5$, which may be the same or different, may be chosen from hydrogen atoms, chlorine atoms, amino groups, (di)alkylamino groups wherein the alkyl part is $C_1$-$C_6$, (di)hydroxy-alkylamino groups wherein the alkyl part is $C_1$-$C_6$, hydroxy groups, linear and branched $C_1$-$C_6$ alkyl groups, and linear and branched $C_1$-$C_6$ alkoxy groups, wherein the alkyl and alkoxy groups may be optionally substituted with at least one entity chosen from hydroxy groups, halogen atoms, $C_1$-$C_6$ alkoxy groups, amino groups, (di)alkylamino groups wherein the alkyl part is $C_1$-$C_6$, and (di)hydroxy-alkylamino groups wherein the alkyl part is $C_1$-$C_6$. For instance, $R_4$ and $R_5$, which may be the same or different, may be chosen from hydrogen atoms, methyl groups, ethyl groups, methoxy groups, ethoxy groups, hydroxy groups, amino groups, dimethylamino groups, dihydroxyethylamino groups, and chlorine atoms.

An is at least one anion chosen from cosmetically acceptable anions, such as those chosen from organic and inorganic anions, and which allow the charge or charges on the compounds of formula (I) to be balanced. For example, the at least one anion can be chosen from halides such as chloride, bromide, fluoride or iodide; hydroxides; sulphates; hydrogen sulphates; alkyl sulphates for which the linear or branched alkyl moiety is $C_1$-$C_6$, such as the methyl sulphate or ethyl sulphate ion; carbonates and hydrogen carbonates; salts of carboxylic acids, such as formate, acetate, citrate, tartrate or oxalate; alkylsulphonates for which the linear or branched alkyl moiety is $C_1$-$C_6$, such as the methylsulphonate ion; arylsulphonates for which the aryl moiety, such as phenyl, is optionally substituted by at least one $C_1$-$C_4$ alkyl radical, such as 4-tolylsulphonate, for example; and alkylsulphonyls such as mesylate.

The compound of formula (I) can be present in the dyeing composition used in the process as disclosed herein, for example, in an amount ranging from 0.001% to 20% by weight, relative to the weight of the dyeing composition, such as ranging from 0.01% to 10% by weight, relative to the weight of the dyeing composition.

The compounds of formula (I) are known per se. For example, those described in U.S. Pat. No. 3,390,948 may be cited.

Another aspect of the present disclosure is the compounds of formula (I'):

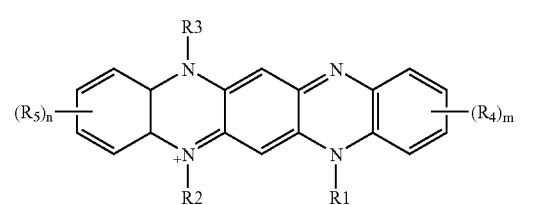

wherein:
R₁, R₂ and R₃, which may be the same or different, are chosen from linear and branched C₁-C₂₄ alkyl groups, C₆-C₃₀ aryl groups, aralkyl groups wherein the aryl part is C₆-C₃₀ and the linear or branched alkyl part is C₁-C₂₄; with the proviso that R₁ and R₃, which may be the same or different, are chosen from alkyl groups comprising at least one hydroxyl group;

R₄ and R₅, which may be the same or different, are chosen from hydrogen atoms, halogen atoms, hydroxy groups, linear and branched C₁-C₂₄ alkyl groups, linear and branched C₁-C₂₄ alkoxy groups, monohydroxy alkoxy groups wherein the alkyl part is linear or branched C₁-C₆, polyhydroxy alkoxy groups wherein the alkyl part is linear or branched C₁-C₆, amino groups optionally substituted with at least one group chosen from linear and branched C₁-C₆ alkyl groups which may be the same or different, optionally substituted with at least one hydroxyl group, thiol groups, alkylthio groups wherein the alkyl part is linear or branched C₁-C₆, carboxyl groups in acid or salt form (with an alkali metal or a substituted or unsubstituted ammonium), alkoxycarbonyl groups wherein the alkyl part is linear or branched C₁-C₆, alkylamide groups wherein the alkyl part is linear or branched C₁-C₆, alkylcarbamyl groups wherein the alkyl part is linear or branched C₁-C₆, cyano groups, nitro groups, sulphonyl groups, alkylsulphonyl groups wherein the alkyl part is linear or branched C₁-C₆, alkylsulphonylamido groups wherein the alkyl part is linear or branched C₁-C₆, C₆-C₃₀ aryl groups optionally substituted with at least one C₁-C₆ alkyl group, and aralkyl groups wherein the aryl part is C₆-C₃₀, optionally substituted with at least one C₁-C₆ alkyl group, and the linear or branched alkyl part is C₁-C₂₄, wherein the alkyl and aryl groups and/or parts are optionally substituted with at least one entity chosen from hydroxyl groups, —SO₃⁻ groups, —COO⁻ groups, halogen atoms, C₁-C₆ alkoxy groups, monohydroxy alkoxy groups wherein the alkyl part is linear or branched C₁-C₆, polyhydroxy alkoxy groups wherein the alkyl part is linear or branched C₁-C₆, amino groups optionally substituted with at least one group chosen from linear and branched C₁-C₆ alkyl groups which may be the same or different, optionally substituted with at least one hydroxyl group, n and m, which may be the same or different, are integers from 0 to 4, An is at least one anion chosen from cosmetically acceptable anions; and p is equal to 0 or 1, so as to respect the electroneutrality of the compound.

For example, the compound of formula (I) may be chosen from one of the formulae (i), (ii) and (iii):

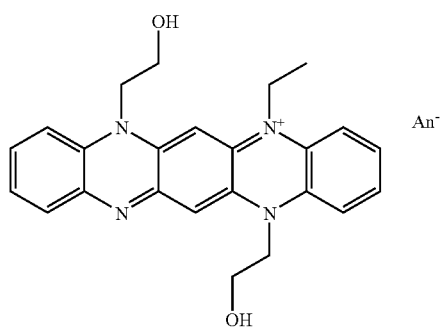

(i)

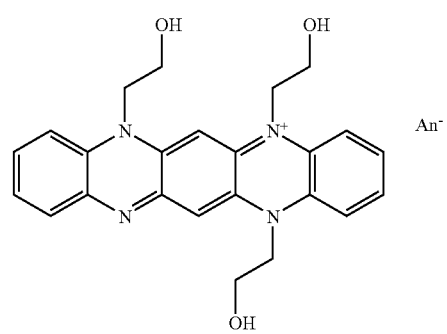

(ii)

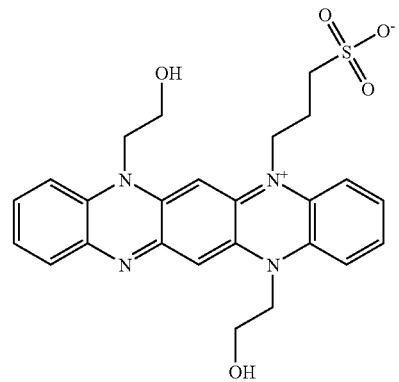

(iii)

These compounds can be obtained conventionally by the person skilled in the art. For example, reference may be made again to the aforementioned U.S. Pat. No. 3,390,948.

As a reactant use may be made, for example, of a compound of the following formula:

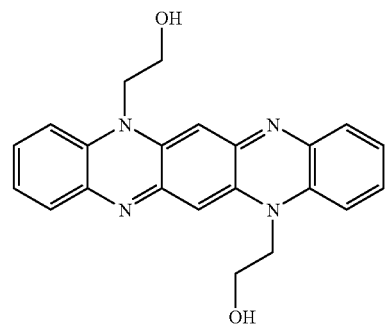

and then a conventional quaternization step may be carried out on this compound.

Still another aspect of the present disclosure is a dyeing composition comprising, as a direct dye, at least one compound of the formula (I), and at least one polymer. The at least one polymer, for example, can be chosen from associative and non-associative thickening polymers, conditioning polymers, and fixing polymers.

As used herein, the term "associative polymers" is understood to mean hydrophilic polymers capable, in an aqueous medium, of reversibly associating with one another or with other molecules. For instance, their chemical structure comprises at least one hydrophilic zone and at least one hydrophobic zone.

The associative polymers present in the composition according to the present disclosure can be chosen from nonionic, anionic, cationic and amphoteric polymers.

Among the associative polyurethane derivatives, non-limiting mention can be made of anionic copolymers obtained by polymerization of:

20% to 70% by weight of an α,β-monoethylenically unsaturated carboxylic acid,

20% to 80% by weight of a non-surfactant α,β-monoethylenically unsaturated monomer different from the foregoing, 0.5 to 60% by weight of a nonionic monourethane which is the product of reaction of a monohydroxylated surfactant with a monoethylenically unsaturated monoisocyanate.

Such associative polyurethanes are, for example, described in European Patent No. 173109, such as in Example 3. For instance, this polymer is a methacrylic acid/methyl acrylate/dimethyl metaisopropenyl benzyl isocyanate terpolymer of ethoxylated behenyl alcohol (40 EO) in 25% aqueous dispersion. This product is offered by the company AMERCHOL under the designation VISCOPHOBE DB1000.

Non-limiting mention can also be made of the cationic associative polyurethanes the family of which is described in French Patent Application No. FR 0009609.

The associative polyurethane derivatives of the present disclosure can also be nonionic polyether polyurethanes. For example, the polymers can simultaneously comprise in their chain hydrophilic sequences most commonly of polyoxyethylenated type and hydrophobic sequences which can be aliphatic sequences alone and/or cycloaliphatic and/or aromatic sequences.

For instance, these polyurethane polyethers can comprise at least two lipophilic hydrocarbon chains comprising from 6 to 30 carbon atoms, separated by a hydrophilic sequence, and the hydrocarbon chains can be side-chains or chains at the end of a hydrophilic sequence. For further instance, it is possible to envisage at least one side-chain. Also, the polymer can comprise a hydrocarbon chain at one end or at both ends of a hydrophilic sequence.

The polyurethane polyethers can have multisequences, for example, in triblock form. The hydrophobic sequences can be at each end of the chain (for example: triblock copolymer with central hydrophilic sequence) or distributed both at the ends and in the chain (multisequence copolymer for example). These same polymers can also be in graft or star form.

The nonionic polyurethane polyethers with fatty chains as used herein can be triblock copolymers wherein the hydrophilic sequence is a polyoxyethylene chain comprising from 50 to 1000 oxyethylene groups.

As examples of nonionic polyurethane polyethers with hydrophobic chains that may be used in the invention, non-limiting mention can be made of Rhéolate 205® with the urea function sold by the company RHEOX or else Rhéolatese 208, 204 or 212, and also Acrysol RM 184® can also be used. The product ELFACOS T210® with a $C_{12}$-$C_{14}$ alkyl chain and the product ELFACOS T212® with a $C_{18}$ alkyl chain from AKZO can also be mentioned in a non-limiting manner, as well as the product DW 1206B® from ROHM & HAAS with a $C_{20}$ alkyl chain and a urethane linkage, offered at 20% dry substance in water.

Solutions or dispersions of these polymers, such as in water or water/alcohol media can also be used. As examples of such polymers, Rhéolate® 255, Rhéolate® 278 and Rhéolate® 244 sold by the company RHEOX can be mentioned in a non-limiting manner. The product DW 1206F and DW 1206J offered by the company ROHM & HMS can also be used.

The polyurethane polyethers usable according to the present disclosure can also be selected from those described in the article by G. Fonnum, J. Bakke and Fk. Hansen—Colloid Polym. Sci 271, 380-389 (1993).

For further non-limiting example, a polyurethane polyether that can be obtained by polycondensation of at least three compounds including (i) at least one polyethylene glycol comprising from 150 to 180 moles of ethylene oxide, (ii) stearyl alcohol or decyl alcohol and (iii) at least one diisocyanate, can also be used. Such polyurethane polyethers are sold, for instance, by the company ROHM & HAAS under the names Aculyn 46® and Aculyn 44®. ACULYN 46® is a polycondensate of polyethylene glycol with 150 or 180 moles of ethylene oxide, stearyl alcohol and methylene bis(4-cyclo-hexyl isocyanate) (SMDI), 15% by weight in a matrix of maltodextrin (4%) and water (81%). ACULYN 44® is a polycondensate of polyethylene glycol with 150 or 180 moles of ethylene oxide, decyl alcohol and methylene bis(4-cyclohexyl isocyanate) (SMDI), 35% by weight in a mixture of propylene glycol (39%) and water (26%).

Among the associative cellulose-derived polymers usable according to the present disclosure, non-limiting mention may be made of:

quaternized cationic celluloses modified with groups comprising at least one hydrophobic chain, such as alkyl, aralkyl or alkaryl groups comprising at least 8 carbon atoms, or mixtures thereof, quaternised cationic hydroxyethylcelluloses modified with groups comprising at least one hydrophobic chain, such as alkyl, aralkyl or alkaryl groups comprising at least 8 carbon atoms, or mixtures thereof.

The alkyl groups derived from the above quaternised celluloses or hydroxyethylcelluloses can comprise, for example, from 8 to 30 carbon atoms. The aryl groups for instance, may be chosen from phenyl, benzyl, naphthyl and anthryl groups. As examples of quaternised alkylhydroxyethylcelluloses with a $C_8$-$C_{30}$ hydrophobic chain, non-limiting mention may be made of the products QUATRISOFT LM 200®, QUATRISOFT LM-X 529-18-A®, QUATRISOFT LM-X 529-18-B® ($C_{12}$ alkyl) and QUATRISOFT LM-X 529-8® ($C_{18}$ alkyl) marketed by the company AMERCHOL and the products CRODACEL QM®, CRODACEL QL® ($C_{12}$ alkyl) and CRODACEL QS® ($C_{18}$ alkyl) marketed by the company CRODA, nonionic cellulose derivatives such as hydroxyethylcelluloses modified with groups comprising at least one hydrophobic chain, such as alkyl, aralkyl or alkaryl groups, or mixtures thereof, and wherein the alkyl groups are, for example, $C_8$-$C_{22}$, such as the product NATROSOL PLUS GRADE 330 CS® ($C_{16}$ alkyls) sold by the company AQUALON, or the product BERMACOLL EHM 100® sold by the company BEROL NOBEL, and cellulose derivatives modified with alkylphenol polyalkylene glycol ether groups, such as the product AMERCELL POLYMER HM-1500® sold by the company AMERCHOL.

Among the associative polyvinyllactams that may be used as disclosed herein, non-limiting mention may be made of those described in French Patent No. FR 0101106.

Terpolymers comprising, by weight, 40 to 95% of monomer (a), 0.1 to 55% of monomer (c) and 0.25 to 50% of monomer (b) can also be used. Such polymers are described, for instance, in the International Patent Application No. WO 00/68282, the particular disclosure related to such polymers which is incorporated herein by reference.

Among the poly(vinyllactam) polymers that may be used as disclosed herein, non-limiting mention can be made of, for example, vinyl pyrrolidone/dimethylaminopropyl-methacrylamide/dodecyl dimethylmethacrylamidopropyl-lammonium tosylate terpolymers, vinylpyrrolidone/dimethyl aminopropylmethacrylamide/cocoyl-dimethylmethacrylamido propyl ammonium tosylate terpolymers, and vinylpyrrolidone/dimethylaminopropyl methacrylamide/lauryldimethylmethacrylamidopropylammonium tosylate or chloride terpolymers.

The associative polyvinyllactam derivatives of the present disclosure can also be nonionic copolymers of vinylpyrrolidone and hydrophobic monomers with hydrophobic chains, as non-limiting examples wherein the following can be mentioned:

the products ANTARON V216® or GANEX V216® (vinylpyrrolidone/hexadecene copolymer) sold by the company I.S.P.

the products ANTARON V220® or GANEX V220® (vinylpyrrolidone/eicosene copolymer) sold by the company I.S.P.

Among the derivatives of associative unsaturated polyacids, that may be used, non-limiting mention can be made of those comprising at least one hydrophilic unit of the olefinic unsaturated carboxylic acid type, such as acrylic, methacrylic and ethacrylic acids and at least one hydrophobic unit of the unsaturated carboxylic acid ($C_{10}$-$C_{30}$) alkyl ester type. Anionic polymers of this type are, for example, described in and can be prepared according to U.S. Pat. Nos. 3,915,921 and 4,509,949. For example, in this type of anionic associative polymer, polymers can be formed from a mixture of monomers comprising:

(i) essentially acrylic acid,
(ii) an alkyl (meth)acrylate comprising 12 to 22 carbon atoms,
(iii) and a crosslinking agent, which is a well known copolymerisable polyethylenic unsaturated monomer, such as diallyl phthalate, allyl (meth)acrylate, divinylbenzene, (poly)ethylene glycol dimethacrylate and methylene-bis-acrylamide.

Among this type of anionic associative polymer, further non-limiting mention can be made of those comprising from 95% to 60% by weight of acrylic acid (hydrophilic unit), 4% to 40% by weight of $C_{10}$-$C_{30}$ alkyl acrylate (hydrophobic unit) and 0% to 6% by weight of crosslinking polymerisable monomer, or indeed those comprising from 96% to 98% by weight of acrylic acid (hydrophilic unit), 1% to 4% by weight of $C_{10}$-$C_{30}$ alkyl acrylate (hydrophobic unit) and 0.1% to 0.6% by weight of crosslinking polymerizable monomer such as those described above. For instance, among the polymers above, the products sold by the company GOODRICH under the trade names PEMULEN TR1®, PEMULEN TR2®, CARBOPOL 1382®can be used, and for example, PEMULEN TR1 ®, and the product sold by the company S.E.P.P.I.C. under the name COATEX SX®.

Among the associative unsaturated polyacid derivatives, non-limiting mention can be made of those comprising among their monomers an α,β-monoethylenic unsaturated carboxylic acid and an ester of an α,β-monoethylenic unsaturated carboxylic acid and an oxyalkylenated fatty alcohol. For example, these compounds may also comprise as a monomer an ester of an α,β-monoethylenic unsaturated carboxylic acid and a $C_1$-$C_4$ alcohol.

A non-limiting example of this type of compound includes, ACULYN 22® sold by the company ROHM & HAAS, which is a methacrylic acid/ethyl acrylate/oxyalkylenated stearyl methacrylate terpolymer. Among the non-associative thickening polymers, these latter type do not comprise a $C_{10}$-$C_{30}$ fatty chain.

Further among the non-associative thickening polymers, non-limiting mention can be made of homopolymers of acrylic acid crosslinked, for example, with an allyl ether of an alcohol of the sugar series, such as, for example, the products sold under the names CARBOPOLS 980, 981, 954, 2984 and 5984 by the company NOVEON or the products sold under the names SYNTHALEN M and SYNTHALEN K by the company 3 VSA can be mentioned.

Still further among the non-associative thickening polymers that can be used as disclosed herein, the crosslinked homopolymers of 2-acrylamido-2-methyl-propanesulphonic acid and the partially or totally neutralized crosslinked acrylamide copolymers thereof can also be mentioned in a non-limiting manner. For example, the homopolymers described in European Patent Application No. EP 815 828, which is incorporated herein by reference. Among the partially or totally neutralized crosslinked copolymers of 2-acrylamido-2-methyl-propanesulphonic acid and acrylamide, non-limiting mention can be made of the product described in Example 1 of European Patent No. EP 503 853, and reference can be made to that document with regard to these polymers. It should be noted that in the case where the compounds are neutralized, this can be done, for instance, by the use of a base such as sodium or potassium hydroxide or an amine.

Also suitable as non-associative thickening polymers are homopolymers of ammonium acrylate or copolymers of ammonium acrylate and acrylamide. As examples of homopolymers of ammonium acrylate, non-limiting mention can be made of the product sold by the company HOECHST under the name MICROSAP PAS 5193. Among the copolymers of ammonium acrylate and acrylamide, non-limiting mention can be made of the product sold under the name BOZEPOL C NOUVEAU, or the product PAS 5193 sold by the company HOECHST. For example, reference can also be made to the description and the preparation of such compounds in French Patent No. FR 2,416,723, and U.S. Pat. Nos. 2,798,053 and 2,923,692.

The homopolymers of dimethylaminoethyl methacrylate quaternized with methyl chloride or copolymers of dimethylaminoethyl methacrylate quaternised with methyl chloride and acrylamide can also be used as non-associative thickening polymers. Among the homopolymers in this family, non-limiting mention can be made of the products sold by the company CIBA-ALLIED COLLOIDS under the names SALCARE 95 and SALCARE 96. Among the copolymers in this family, non-limiting mention can be made of the product SALCARE SC92 sold by CIBA-ALLIED COLLOIDS or the product PAS 5194 sold by HOECHST. For example, these polymers are described and prepared in the European Patent No. EP 395 282, to which reference can be made.

Also suitable for use as disclosed herein are non-modified nonionic guar gums such as those sold by the company UNIPECTINE under the name VIDOGUM GH 175 and by the company MEYHALL under the name JAGUAR C. It is also possible to use nonionic guar gums modified with $C_1$-$C_6$ hydroxyalkyl groups (such as hydroxymethyl, hydroxyethyl, hydroxypropyl and hydroxybutyl). Among such nonionic guar gums modified with hydroxyalkyl groups, non-limiting mention can be made of, for example, those sold by the company MEYHALL under the trade names JAGUAR HP8, JAGUAR HP60 and JAGUAR HP120, JAGUAR DC 293 and JAGUAR HP 105 or by the company AQUALON under the name GALACTASOL 4H$_4$FD2.

Also suitable are biopolysaccharide gums of microbial origin, such as for example scleroglucan or xanthan gums, gums derived from plant exudates such as gum arabic, Ghatti gums, Karaya and Tragacanth gums, hydroxypropyl or carboxymethyl celluloses, pectins and alginates. Such compounds are, for instance, described in the work by Robert L. DAVIDSON entitled "Handbook of Water soluble gums and resins", published by McGraw Hill Book Company (1980).

The at least one associative or non-associative thickening polymer can be present in the dyeing composition in an amount ranging from 0.01 to 10% by weight, such as from 0.1 to 5% by weight, relative to the weight of the dyeing composition.

As indicated above, the composition according to the present disclosure can also comprise at least one polymer chosen from conditioning polymer and fixing polymers.

As used herein, the term "conditioning agent" is understood to mean any agent having the function of improving the cosmetic properties of keratinic materials such as the hair, such as the softness, disentangling, feel, shine and static electricity.

The conditioning polymers can be chosen from cationic polymers and cationic or nonionic polyorganosiloxanes.

As used herein, the term "cationic polymer" is understood to mean any polymer comprising cationic groups and/or groups ionizable to give cationic groups.

The cationic polymers that may be used as disclosed herein can be chosen from all those already known as such for their ability to improve the cosmetic properties of hair treated with detergent compositions. For instance, non-limiting mention can be made of those described in the European Patent Application No. EP 0 337 354, and French Patent Application Nos. FR 2,270,846, FR 2,383,660, FR 2,598,611, FR 2,470,596 and FR 2,519,863.

For example, the cationic polymers may be chosen from those which comprise units comprising primary, secondary, tertiary and/or quaternary amine groups which are part of the principal macromolecular chain, or else are borne by side groups directly linked thereto.

Among the cationic polymers that may be used, non-limiting mention can be made of polymers of the polyamine, polyaminoamide and quaternary polyammonium type. These are known products. The polymers of the polyamine, polyaminoamide and quaternary polyammonium type that can be used in the compositions of the present disclosure are those described in the French Patent Nos. FR 2,505,348 and FR 2,542,997. Among these polymers, non-limiting mention can be made of:

(1) homopolymers or copolymers derived from acrylic or methacrylic esters or amides and comprising at least one unit of the following formulae:

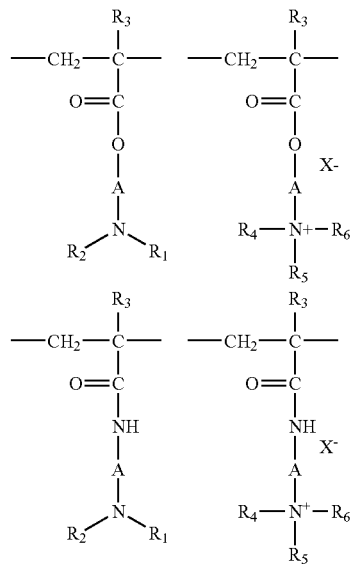

wherein:
$R_3$ which may be the same or different, are chosen from hydrogen atoms and $CH_3$ groups,
A which may be the same or different, are chosen from linear and branched alkyl groups, comprising from 1 to 6 carbon atoms, such as 2 to 3 carbon atoms, and hydroxyl groups comprising from 1 to 4 carbon atoms,
$R_4$, $R_5$ and $R_6$ which may be the same or different, are chosen from alkyl groups comprising from 1 to 18 carbon atoms, such as alkyl groups comprising from 1 to 6 carbon atoms, and benzyl groups,
$R_1$ and $R_2$ which may be the same or different, are chosen from hydrogen atoms oand alkyl groups comprising from 1 to 6 carbon atoms, such as methyl and ethyl groups, and
$X^-$ is an anion chosen from those derived from inorganic and organic acids, such as a methosulphate anion, and halides such as chloride or bromide.

The copolymers of the family (1) can, in addition, comprise at least one unit deriving from comonomers selected within the family of the acrylamides, methacrylamides, diacetone-acrylamides, acrylamides and methacrylamides substituted on the nitrogen atom with $C_1$-$C_4$ lower alkyl groups, groups derived from acrylic or methacrylic acids or esters thereof, vinyllactams such as vinylpyrrolidone or vinylcaprolactam, and vinyl esters.

Among the copolymers of the family (1), non-limiting mention can be made of the following:
copolymers of acrylamide and dimethylaminoethyl methacrylate quaternized with dimethyl sulphate or with a methyl halide, such as that sold by the company HERCULES under the name HERCOFLOC®,
copolymers of acrylamide and methacryloyloxyethyltrimethlyammonium chloride, described, for example, in European Patent Application No. EP-A-080975 and sold by the company CIBA-GEIGY under the name BINAQUAT® P 100,
the copolymer of acrylamide and methacryloyloxyethyltrimethylammonium methosulphate sold by the company HERCULES under the name RETEN®, vinylpyrrolidone/quaternised or non-quaternised dialkylaminoalkyl acrylate or methacrylate copolymers, such as the products sold by the company ISP under the name GAFQUAT®, for example GAFQUAT® 734 or GAFQUAT® 755, or indeed the products called COPOLYMER 845, 958 and 937. These polymers are described in detail in French Patent Nos. FR 2,077,143 and FR 2,393,573, dimethylaminoethyl methacrylate/vinylcaprolactam/vinylpyrrolidone terpolymers such as the product sold by the company ISP under the name GAFFIX® VC 713, vinylpyrrolidone/methacrylamidopropyl-di-methylamine copolymers marketed, for instance, by ISP under the name STYLEZE® CC 10, and vinylpyrrolidone/quaternised dimethylaminopropyl methacrylamide copolymers, such as the product sold by the company ISP under the name GAFQUAT® HS 100.

(2) Cellulose ether derivatives comprising quaternary ammonium groups described in French Patent No. FR 1,492,597, and, for example, the polymers marketed by the company Union Carbide Corporation under the names "JR" (JR 400, JR 125, JR 30M) or "LR" (LR 400, LR 30M). These polymers are also defined in the CTFA dictionary as quaternary ammonium compounds of hydroxyethylcellulose that has reacted with an epoxide substituted with a trimethylammonium group.

(3) Cationic cellulose derivatives, such as copolymers of cellulose or derivatives of cellulose grafted with a water-soluble quaternary ammonium monomer, and described, for instance, in U.S. Pat. No. 4,131,576, such as the hydroxyalkylcelluloses, such as the hydroxymethyl-, hydroxyethyl- or hydroxypropylcelluloses grafted, for example, with a methacryloylethyl-trimethylammonium, methacrylamidopropyltrimethylammonium or dimethyldiallyl-ammonium salt. The products marketed which correspond to this definition include, for example, the products sold by the company National Starch under the name Celquat® L 200 and Celquat® H 100.

(4) The cationic polysaccharides described, for example, U.S. Pat. Nos. 3,589,578 and 4,031,307, such as guar gums comprising cationic trialkylammonium groups. For example, guar gums modified with a 2,3-epoxypropyltrimethylammonium salt, such as the chloride are used. Such products are marketed, for instance, by the company MEYHALL under the trade names JAGUAR® C13 S, JAGUAR® C15, JAGUAR® C17 or JAGUAR® C162.

(5) Polymers comprising piperazinyl units and divalent straight or branched chain alkylene or hydroxyalkylene groups, optionally interrupted by oxygen, sulphur or nitrogen atoms or by aromatic or heterocyclic rings, and the products of oxidation and/or quaternization of these polymers. Such polymers are, for example, described in French Patent Nos. FR 2,162,025 and FR 2,280,361.

(6) Water-soluble polyaminoamides, prepared for example, by polycondensation of an acidic compound with a polyamine. These polyaminoamides can be crosslinked with an epihalohydrin, a diepoxide, a dianhydride, an unsaturated dianhydride, a bis-unsaturated derivative, a bis-halohydrin, a bis-azetidinium, a bis-haloacyldiamine, an alkyl bis-halide or else by an oligomer resulting from the reaction of a bifunctional compound reactive towards a bis-halohydrin, a bis-azetidinium, a bis-haloacyidiamine, an alkyl bis-halide, an epihalohydrin, a diepoxide or a bis-unsaturated derivative, the crosslinking agent being used in an amount ranging from 0.025 moles to 0.35 moles per amino group of the polyaminoamide. These polyaminoamides can be alkylated or, if they comprise at least one tertiary amine function, quaternized. Such polymers are, for example, described in French Patent Nos. FR 2,252,840 and FR 2,368,508.

(7) Derivatives of polyaminoamides resulting from the condensation of polyalkylenes-polyamines with polycarboxylic acids, followed by alkylation with bifunctional agents. For example, non-limiting mention can be made of adipic acid/dialkylaminohydroxyalkyl-dialkylenetriamine polymers, wherein the alkyl group comprises from 1 to 4 carbon atoms, such as methyl, ethyl or propyl groups, and the alkylene group comprises from 1 to 4 carbon atoms, such as the ethylene group. Such polymers are, for example, described in French Patent No. FR 1,583,363. Among these derivatives, non-limiting mention can be made of the adipic acid/dimethylaminohydroxypropyl-diethylene-triamine polymers sold by the company Sandoz under the name Cartaretine® F, F4 or F8.

(8) Polymers obtained by reaction of a polyalkylenepolyamine comprising two primary amine groups and at least one secondary amine group with a dicarboxylic acid selected from diglycolic acid and the saturated aliphatic dicarboxylic acids comprising from 3 to 8 carbon atoms, the molar ratio of the polyalkylene-polyamine to the dicarboxylic acid ranging from 0.8:1 to 1.4:1. The polyaminoamide resulting from this reaction is then reacted with epichlorhydrin in a molar ratio of epichlorhydrin relative to the secondary amine group of the polyaminoamide ranging from 0.5:1 to 1.8:1. Such polymers are, for example, described in U.S. Pat. Nos. 3,227,615 and 2,961,347. Polymers of this type are, for example, marketed by the company Hercules Inc. under the name Hercosett® 57 or else by the company Hercules under the name PD 170 or Delsette® 101 in the case of the copolymer of adipic acid/epoxypropyl-diethylene-triamine.

(9) Cyclopolymers of alkyldiallylamine or dialkyldiallylammonium such as homopolymers or copolymers comprising, as the main constituent of the chain, units chosen from formulae (Va) and (Vb):

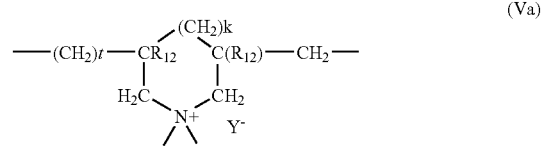

(Va)

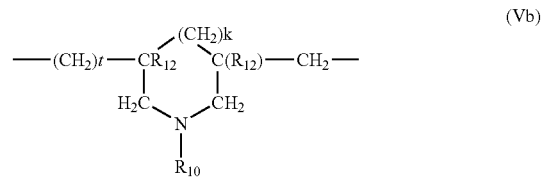

(Vb)

wherein k and t are equal to 0 or 1, the sum k+t being equal to 1, $R_{12}$ is chosen from a hydrogen atom and methyl groups, $R_{10}$ and $R_{11}$, which may be the same or different, are chosen from alkyl groups comprising from 1 to 22 carbon atoms, $C_{1-5}$ hydroxyalkyl groups and $C_1$-$C_4$ lower amidoalkyl groups, or, alternatively, $R_{10}$ and $R_{11}$ can jointly form, with the nitrogen atom to which they are attached, heterocyclic groups, such as piperidinyl or morpholinyl, Y⁻ is an anion such as bromide, chloride, acetate, borate, citrate, tartrate, bisulphate, bisulphite, sulphate or phosphate.

These polymers are described, for example, in French Patent No. FR 2,080,759 and the additional patent thereto 2,190,406.

Among the polymers defined above, non-limiting mention can be made of the homopolymer of dimethyldiallylammonium chloride sold by the company CALGON under the name MERQUAT® 100 (and its homologues of low weight average molecular weight) and the copolymers of diallyldimethylammonium chloride and acrylamide marketed under the name MERQUAT® 550.

(10) Quaternary diammonium polymers comprising recurring units of formula (VI):

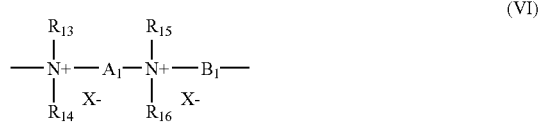

wherein:

$R_{13}$, $R_{14}$, $R_{15}$ and $R_{16}$, which may be the same or different, are chosen from aliphatic, alicyclic and arylaliphatic groups comprising from 1 to 20 carbon atoms, and lower aliphatic hydroxyalkyl groups, or else $R_{13}$, $R_{14}$, $R_{15}$ and $R_{16}$, together or separately, can form, with the nitrogen atoms to which they are attached, heterocycles optionally comprising a second hetero atom other than nitrogen, or alternatively, $R_{13}$, $R_{14}$, $R_{15}$ and $R_{16}$ are chosen from linear and branched $C_{1-6}$ alkyl groups, substituted with a nitrile, ester, acyl, amide, —CO—O—$R_{17}$-D and —CO—NH—$R_{17}$-D groups, where $R_{17}$ is an alkylene group and D a quaternary ammonium group, $A_1$ and $B_1$ are chosen from linear and branched, saturated and unsaturated, polymethylene groups comprising from 2 to 20 carbon atoms, which may comprise, bound or interposed in the main chain, at least one entity chosen from aromatic rings, oxygen atoms, sulphur atoms, and sulphoxide, sulphone, disulphide, amino, alkylamino, hydroxyl, quaternary ammonium, ureido, amide and ester groups, and $X^-$ is an anion derived from an inorganic or organic acid, wherein $A_1$, $R_{13}$ and $R_{15}$ can form a piperazine ring with the two nitrogen atoms to which they are attached, further, if $A_1$ is chosen from linear and branched, saturated and unsaturated alkylene and hydroxyalkylene groups, then $B_1$ can also be chosen from groups of:

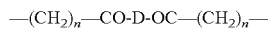

wherein D is chosen from a) glycol residues of formula —O—Z—O—, where Z is chosen from linear and branched hydrocarbon groups, and groups of formulae:

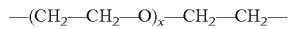

and

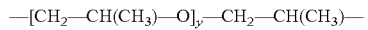

where x and y are any whole number from 1 to 4 representing a defined and unique degree of polymerisation or any number from 1 to 4 representing a mean degree of polymerisation, b) bis-secondary diamine residues, such as a piperazine derivatives, c) bis-primary diamine residues of formula —NH—Y—NH—, wherein Y is chosen from linear and branched hydrocarbon groups, and divalent —$CH_2$—$CH_2$—S—S—$CH_2$—$CH_2$— groups, and d) ureylene groups of formula —NH—CO—NH—.

For example, $X^-$ may be an anion chosen from chloride and bromide.

These polymers have a number average molecular weight ranging from 1,000 to 100,000. Polymers of this type are described, for example, in French Patent Nos. FR 2,320,330, FR 2,270,846, FR 2,316,271, FR 2,336,434 and FR 2,413,907 and U.S. Pat. Nos. 2,273,780, 2,375,853, 2,388,614, 2,454,547, 3,206,462, 2,261,002, 2,271,378, 3,874,870, 4,001,432, 3,929,990, 3,966,904, 4,005,193, 4,025,617, 4,025,627, 4,025,653, 4,026,945 and 4,027,020.

For instance, polymers which comprise recurrent units of formula (VII):

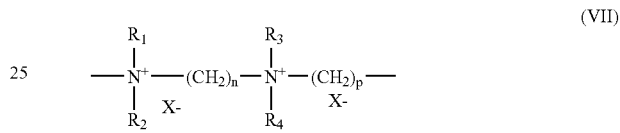

wherein $R_1$, $R_2$, $R_3$ and $R_4$, which can be the same or different, are chosen from alkyl and hydroxyalkyl groups comprising from 1 to 4 carbon atoms, n and p are integers ranging from 2 to about 20 and $X^-$ is an anion derived from an inorganic or organic acid can be used.

For example, in formula (VII), $R_1$, $R_2$, $R_3$ and $R_4$ may be chosen from methyl groups, with n equal to 3, p equal to 6 and X may be a Cl, which is called hexadimethrine chloride (CTFA).

(11) Quaternary polyammonium polymers, comprising units of formula (VIII):

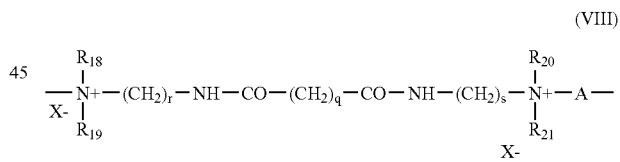

wherein:

$R_{18}$, $R_{19}$, $R_{20}$ and $R_{21}$, which may be the same or different, are chosen from hydrogen atoms, and methyl, ethyl, propyl, β-hydroxyethyl, β-hydroxypropyl and —$CH_2CH_2$(O$CH_2CH_2$)$_p$OH groups, where p is an integer ranging from 0 to 6, with the proviso that $R_{18}$, $R_{19}$, $R_{20}$ and $R_2$, are not all simultaneously hydrogen atoms, r and s, which may be the same or different, are integers ranging from 1 to- 6, q is an integer ranging from 0 to 34, $X^-$ is an anion such as a halide, and A is chosen from dihalide groups and —$CH_2$—$CH_2$—O—$CH_2$—$CH_2$—.

Such compounds are, for example, described in European Patent Application No. EP-A-122,324. Among these, for example, non-limiting mention can be made of the products Mirapol® A 15, Mirapol® AD1, Mirapol® AZ1 and Mirapol® 175 sold by the company Miranol.

(12) Quaternary polymers of vinylpyrrolidone and vinylimidazole such as, for example, the products marketed by the company B.A.S.F. under the names Luviquat® FC 905, FC 550 and FC 370. For instance, the copolymers of vinylpyrrolidone and methylvinylimidazolium chloride can be mentioned in a non-limiting manner.

(13) Polyamines such as the Polyquart® H sold by HENKEL, referred to under the name of POLYETHYLENEGLYCOL (15) TALLOW POLYAMINE in the CTFA dictionary.

(14) Crosslinked or non-crosslinked polymers of methacryloyloxy-$(C_{1-4})$-alkyltrialkyl-$(C_{1-4})$-ammonium salts, such as the polymers obtained by homopolymerisation of dimethylamino-ethyl methacrylate quaternised with methyl chloride, or by copolymerisation of acrylamide and dimethylaminoethyl methacrylate quaternised with methyl chloride, the homopolymerisation or copolymerisation being followed by crosslinking with an olefinically unsaturated compound, such as methylene-bisacrylamide. For example, a crosslinked acrylamide/methacryloyloxyethyl-trimethylammonium chloride copolymer (20/80 by weight) in the form of a dispersion comprising 50% by weight of the copolymer in mineral oil can be used. This dispersion is marketed by the company ALLIED COLLOIDS under the name SALCARE® SC 92. A crosslinked homopolymer of methacryloyloxyethyl-trimethylammonium chloride comprising about 50% by weight of the homopolymer in mineral oil or in a liquid ester can also be used. These dispersions are marketed by the company ALLIED COLLOIDS under the names SALCARE® SC 95 and SALCARE® SC 96.

Other cationic polymers usable in the context of the present disclosure are cationic proteins or hydrolyzates of cationic proteins, polyalkyleneimines, such as polyethyleneimines, polymers conmprising vinylpyridine or vinylpyridinium units, condensates of polyamines and epichlorhydrin, quaternary polyureylenes and cationic derivatives of chitin.

Aminated and non-aminated, such as non-volatile polyorganosiloxanes (either organosiloxanes or silicones), can also be used as a conditioning agent. They can, for instance, take the form of oils, waxes, resins or gums.

Non-limiting mention may be made of the polyalkylsiloxanes, polyarylsiloxanes, polyalkylarylsiloxanes, silicone gums and resins, polyorganosiloxanes modified with organic functional groups, and mixtures thereof.

These silicones for example, can be chosen from polyalkylsiloxanes among which non-limiting mention may be made of the polydimethylsiloxanes with trimethylsilyl terminal groups having a viscosity ranging from $5 \times 10^{-6}$ to 2.5 $m^2$/sec at 25° C., such as $1 \times 10^{-5}$ to 1 $m^2$/sec. The viscosity of the silicones is for example measured at 25° C. in accordance with the standard ASTM 445 Appendix C.

Among these polyalkylsiloxanes, without limitation, the following commercial products can be mentioned:

Silbione® oils of the 47 and 70,047 range or the Mirasil® oils marketed by Rhodia Chimie such as for example the oil 70,047 V 500,000;

the oils of the Mirasil range marketed by the company Rhodia Chimie;

the oils of the 200 range from the company Dow Corning such as, for instance, DC200 of viscosity 60,000 cSt ($mm^2$/sec);

the Viscasil® oils from General Electric and certain oils of the SF ranges (SF 96, SF 18) from General Electric.

Polydimethylsiloxanes with dimethylsilanol terminal groups (Dimethiconol according to the CTFA nomenclature) such as the oils of the 48 range from the company Rhodia Chimie, but also the products marketed by the company Goldschmidt under the names "Abil® Wax 9800 and 9801" which are poly($C_1$-$C_{20}$)alkylsiloxanes may also be used.

The polyalkylarylsiloxanes can also be used, for example, those selected from the linear and/or branched polydimethyl methylphenylsiloxanes and polydimethyl diphenylsiloxanes with a viscosity ranging from $1 \times 10^{-5}$ to $5 \times 10^{-2}$ $m^2$/sec at 25° C.

Among these polyalkylarylsiloxanes, the products marketed under the following names can for example be mentioned, in a non-limiting manner:

the Silbione oils of the 70,641 range from Rhodia Chimie, the oils of the Rhodorsil 70,633 and 763 ranges from Rhodia Chimie, the oil Dow Corning 556 Cosmetic Grad Fluid from Dow Corning, the silicones of the PK range from Bayer such as the product PK20, the silicones of the PN and PH ranges from Bayer such as the products PN1000 and PH1000, certain oils of the SF ranges from General Electric such as SF 1023, SF 1154, SF 1250 and SF 1265.

The silicone gums usable according to the present disclosure include, for example, polydiorganosiloxanes having high number average molecular weights ranging from 200,000 to 1,000,000 used alone or mixed in a solvent. This solvent can be selected from the volatile silicones, polydimethylsiloxane oils (PDMS), poly-phenylmethylsiloxane oils (PPMS), isoparaffins, poly-isobutylenes, methylene chloride, pentane, dodecane, tridecanes or mixtures thereof.

For further example, non-limiting mention can be made of the following products of the polydimethylsiloxane type: polydimethyl-siloxane/methylvinylsiloxane gums, polydimethylsiloxane/diphenylsiloxanes, polydimethyl-siloxane/phenylmethylsiloxanes, and polydimethylsiloxane/diphenylsiloxane/methylvinyl-siloxanes.

Among the products that can be used according to the present disclosure, non-limiting mention can be made of mixtures such as:

mixtures formed from a polydimethylsiloxane hydroxylated at the chain end (called dimethiconol according to the CTFA dictionary nomenclature) and a cyclic polydimethylsiloxane (called cyclomethicone according to the CTFA dictionary nomenclature) such as the product Q2 1401 marketed by the company Dow Corning;

mixtures formed from a polydimethylsiloxane gum with a cyclic silicone such as the product SF 1214 Silicone Fluid from the company General Electric, this product is a SF 30 gum corresponding to a dimethicone, having a number average molecular weight of 500,000 dissolved in the oil SF 1202 Silicone Fluid corresponding to decamethylcyclopentasiloxane.

mixtures of two PDMS of different viscosities, for instance, a PDMS gum and a PDMS oil, such as the product SF 1236 from the company General Electric. The product SF 1236 is a mixture of a gum SE 30 defined above having a viscosity of 20 $m^2$/sec and of an oil SF 96 of viscosity $5 \times 10^{-6}$ $m^2$/sec. This product can comprise, for example, 15% of gum SE 30 and 85% of an oil SF 96.

The organopolysiloxane resins usable as disclosed herein are crosslinked siloxane systems comprising the units: $R_2SiO_{2/2}$, $R_3SiO_{1/2}$, $RSiO_{3/2}$ and $SiO_{4/2}$ wherein R is chosen from hydrocarbon groups comprising from 1 to 16 carbon atoms and phenyl groups. In one embodiment of the present disclosure, R is chosen from $C_1$-$C_4$ lower alkyl groups, such as methyl, and phenyl groups.

Among these resins, non-limiting mention can be made of the product marketed under the name "Dow Corning 593" or those marketed by the company General Electric under the names "Silicone Fluid SS 4230 and SS 4267" and which are silicones of dimethyl/trimethylsiloxane structure. The resins of the trimethylsiloxysilicate type marketed in particular by the company Shin-Etsu under the names X22-4914, X21-5034 and X21-5037 can also be mentioned in a non-limiting manner.

The organo-modified silicones usable according to the present disclosure are silicones such as defined above and comprising in their structure at least one organic functional group attached via a hydrocarbon group. These organic functional groups are different from the amine groups.

Among the organo-modified silicones different from those of formulae (I) or (II), non-limiting mention may be made of the polyorganosiloxanes comprising:

polyethyleneoxy and/or polypropyleneoxy groups optionally comprising $C_6$-$C_{24}$ alkyl groups such as the products called dimethicone copolyol marketed by the company Dow Corning under the name DC 1248 and the ($C_{12}$) alkyl methicone copolyol marketed by the company Dow Corning under the name Q2 5200;

thiol groups, such as the products marketed by Genesee under the names "GP 72 A" and "GP 71";

alkoxylated groups, such as the product marketed under the name "Silicone Copolymer F-755" by SWS Silicones and Abil Wax 2428, 2434 and 2440 by the company Goldschmidt;

hydroxylated groups, such as the polyorganosiloxanes with hydroxyalkyl groups described in French Patent No. FR 8,516,334;

acyloxyalkyl groups, such as for example polyorganosiloxanes described in U.S. Pat. No. 4,957,732;

anionic groups of the carboxylic type, such as for example, the products described in European Patent No. EP 186507 by the company Chisso Corporation, or of the alkylcarboxylic type such as those present in the product X-22-3701 E from the company Shin-Etsu, 2-hydroxyalkylsulphonate or 2-hydroxyalkylthiosulphate such as the products marketed by the Goldschmidt company under the names "Abil S201" and "Abil S255."

According to the present disclosure, silicones comprising a polysiloxane portion and a portion made up of a non-silicone organic chain, one of the two portions constituting the main chain of the polymer the other being grafted onto the main chain, can also be used. These polymers are for example described in European Patent Nos. EP 412 704, EP 412 707, EP 640 105 and EP 582152, International Patent Application Nos. WO 95/00578, and WO 93/23009, and U.S. Pat. Nos. 4,693,935, 4,278,571 and 4,972,037. For example, these polymers may be chosen from anionic and nonionic polymers.

Other non-limiting examples of grafted silicone polymers include, for example, the polydimethylsiloxanes (PDMS) onto which are grafted, via a connecting linkage of the thiopropylene type, mixed polymer units of the poly(meth) acrylic acid type and of the alkyl poly(meth)acrylate type and polydimethylsiloxanes (PDMS) onto which are grafted, via a connecting linkage of the thiopropylene type, polymer units of the isobutyl poly(meth)acrylate type.

It should be noted that the silicones can also be used in the form of emulsions, nanoemulsions or microemulsions.

As used herein, the term "fixing polymers" is understood to mean any polymer making it possible to impart a shape to the hair and/or to maintain it.

For example, the fixing polymers capable of being used as disclosed herein can be chosen from anionic, amphoteric and nonionic polymers and mixtures thereof.

The fixing polymers can be soluble in the cosmetically acceptable medium or insoluble in that same medium and used in that case in the form of dispersions of solid or liquid particles of polymer (latex or pseudolatex).

The anionic fixing polymers used as disclosed herein can be polymers comprising groups derived from carboxylic, sulphonic or phosphoric acid and have a number average molecular weight ranging from 500 to 5,000,000.

The carboxylic groups are contributed by unsaturated mono or dicarboxylic acid monomers such as those corresponding to the formula:

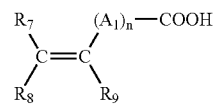

wherein n is an integer from 0 to 10, $A_1$ is chosen from methylene groups, optionally linked to the carbon atom of the unsaturated group, or to the adjacent methylene group when n is greater than 1, via a hetero atom such as oxygen or sulphur, $R_7$ is chosen from a hydrogen atom, and phenyl and benzyl groups, $R_8$ is chosen from a hydrogen atom and lower alkyl and carboxyl groups, and $R_9$ is chosen from a hydrogen atom, lower alkyl groups, and —$CH_2$—COOH, phenyl and benzyl groups. In this formula, a lower alkyl group means for example a group comprising from 1 to 4 carbon atoms, such as methyl and ethyl groups.

Among the fixing anionic polymers with carboxylic groups, that can be used as disclosed herein, non-limiting mention can be made of:

A) Homo- or copolymers of acrylic or methacrylic acid or salts thereof, such as the products sold under the names VERSICOL® E or K by the company ALLIED COLLOID and ULTRAHOLD® by the company BASF, copolymers of acrylic acid and acrylamide and sodium salts of polyhydroxycarboxylic acids.

B) Copolymers of acrylic or methacrylic acid with a monoethylenic monomer such as ethylene, styrene, vinyl esters, esters of acrylic or methacrylic acid, optionally grafted onto a polyalkylene glycol such as polyethylene glycol, and optionally crosslinked. Such polymers are described for example, in French Patent No. 1,222,944 and German Patent Application No. 2,330,956, the copolymers of this type comprising in their chain an acrylamide unit which may be N-alkylated and/or hydroxyalkylated such as are described, for instance, in Luxembourg Patent Application Nos. 75370 and 75371. Non-limiting mention can also be made of the copolymers of acrylic acid and $C_1$-$C_4$ alkyl methacrylate and the terpolymers of vinylpyrrolidone, acrylic acid and $C_1$-$C_{20}$ alkyl, for example lauryl, methacrylate, such as the product marketed by the company ISP under the name ACRYLIDONE® LM and the methacrylic acid/ethyl acrylate/tert-butylacrylate terpolymers-such as the product marketed by the company BASF under the name LUVIMER® 100P.

C) Copolymers derived from crotonic acid, such as those comprising in their chain vinyl acetate or propionate units, and optionally other monomers such as the allyl or methallyl esters, vinyl ether or vinyl ester of a saturated, linear or branched carboxylic acid of long hydrocarbon chain, such as those comprising at least 5 carbon atoms, these polymers optionally grafted and crosslinked, or else another vinyl, allyl or methallyl monomer ester of an α- or β-cyclic carboxylic acid. Such polymers are described inter alia in French Patent Nos. 1,222,944, 1,580,545, 2,265,782, 2,265,781, 1,564,110 and 2,439,798. A commercial product falling within this class is the resin 28-29-30 marketed by the company National Starch.

D) Copolymers derived from monounsaturated $C_4$-$C_8$ carboxylic acids or anhydrides chosen from:

copolymers comprising (i) at least one maleic, fumaric and/or itaconic acids or anhydrides and (ii) at least one monomer chosen from the vinyl esters, vinyl ethers, vinyl halides, phenylvinyl derivatives, acrylic acid and esters thereof, the anhydride groups of these copolymers being optionally monoesterified or monoamidated. Such polymers are, for example, described in U.S. Pat. Nos. 2,047,398, 2,732,248 and 2,102,113 and Great Britain Patent No. 839805. Commercial products include, for instance, those sold by the company ISP under the names GANTREZ® AN or ES.

copolymers comprising (i) at least one maleic, fumaric and/or itaconic units and (ii) at least one monomer chosen from allyl and methallyl esters optionally comprising at least one acrylamide, methacrylamide, α-olefin, acrylic or methacrylic ester, acrylic or methacrylic acid or vinylpyrrolidone groups in their chain, the anhydride groups of these copolymers being optionally monoesterified or monoamidated. These polymers are for example described in French patents Nos. 2,350,384 and 2,357,241.

E) Polyacrylamides comprising carboxylate groups.

The polymers comprising sulphonic groups are polymers comprising vinylsulphonic, styrene-sulphonic, naphthalene-sulphonic or acrylamide-alkylsulphonic units.

These polymers can, for example, be chosen from:

salts of polyvinylsulphonic acid having a molecular weight ranging from 1,000 to 100,000, and copolymers with an unsaturated comonomer such as acrylic or methacrylic acids and esters thereof, and also acrylamide and derivatives thereof, vinyl ethers and vinylpyrrolidone.

salts of polystyrene-sulphonic acid such as the sodium salts sold for example by National Starch under the name Flexan® 130. These compounds are described in French Patent No. FR 2,198,719.

salts of polyacrylamide-sulphonic acids such as those mentioned in U.S. Pat. No. 4,128,631, for instance, polyacrylamidoethylpropanesulphonic acid.

According to the present disclosure, among the anionic fixing polymers mentioned above, further non-limiting mention can be made of copolymers of acrylic acid such as the acrylic acid/ethyl acrylate/N-tert. butylacrylamide terpolymers sold for instance, by the company BASF under the name ULTRAHOLD® STRONG, copolymers derived from crotonic acid such as the vinyl acetate/vinyltertbutylbenzoate/crotonic acid terpolymers and the crotonic acid/vinyl acetate/vinyl neododecanoate terpolymers sold for example, by the company NATIONAL STARCH under the name Resin 28-29-30, the polymers derived from maleic, fumaric and/or itaconic acids or anhydrides with vinyl esters, vinyl ethers, vinyl halides, phenylvinyl derivatives, and acrylic acid and esters thereof such as the methyl vinyl ether/ monoesterified maleic anhydride copolymers sold by the company ISP under the name GANTREZ®, the copolymers of methacrylic acid and methyl methacrylate sold by the company ROHM PHARMA under the name EUDRAGIT® L, the copolymers of methacrylic acid and ethyl acrylate sold by the company BASF under the name LUVIMER® MAEX or MAE and the vinyl acetate/crotonic acid copolymers and the vinyl acetate/crotonic acid copolymers grafted with polyethylene glycol sold by the company BASF under the name ARISTOFLEX® A.

Still further non-limiting mention can be made of anionic fixing polymerschosen from the methyl vinyl ether/monoesterified maleic anhydride copolymers sold by the company ISP under the name GANTREZ® ES 425, the acrylic acid/ethyl acrylate/N-tertbutylacrylamide terpolymers sold by the company BASF under the name ULTRAHOLD® STRONG, the copolymers of methacrylic acid and methyl methacrylate sold by the company ROHM PHARMA under the name EUDRAGIT® L, the vinyl acetate/vinyl tertbutyl benzoate/crotonic acid terpolymers and the crotonic acid/ vinyl acetate/vinyl neododecanoate terpolymers sold by the company NATIONAL STARCH under the name Resin 28-29-30, the copolymers of methacrylic acid and ethyl acrylate sold by the company BASF under the name LUVIMER® MAEX or MAE, and the vinylpyrrolidone/ acrylic acid/lauryl methacrylate terpolymers sold by the company ISP under the name ACRYLIDONE® LM.

Amphoteric fixing polymers that can be used according to the present disclosure can be chosen from polymers comprising units B and C randomly distributed in the polymer chain where B is a unit derived from a monomer comprising at least one basic nitrogen atom and C is a unit derived from an acid monomer comprising at least one group chosen from carboxylic and sulphonic groups, or else B and C can be chosen from groups derived from zwitterionic monomers of carboxybetaines and sulphobetaines; B and C can also be chosen from cationic polymer chains comprising primary, secondary, tertiary or quaternary amine groups, wherein at least one of the amine groups bears a carboxylic or sulphonic group attached via a hydrocarbon group, or else B and C are part of a chain with an ethylene-α,β-dicarboxylic unit wherein one of the carboxylic groups has been reacted with a polyamine comprising at least one amine group chosen from primary and secondary amine groups.

Non-limiting examples of the amphoteric fixing polymers as described herein include:

(1) Polymers resulting from the copolymerization of a monomer derived from a vinyl compound bearing a carboxylic group such as, for instance, acrylic acid, methacrylic acid, maleic acid or alpha-chloracrylic acid, and from a basic monomer derived from a substituted vinyl compound comprising at least one basic atom, such as, for instance, the dialkylaminoalkylmethacrylates and acrylates and the dialkylaminoalkylmethacrylamides and acrylamides. Such compounds are described in U.S. Pat. No. 3,836,537.

(2) Polymers comprising units derived:
 a) from at least one monomer selected from the acrylamides or the methacrylamides substituted with an alkyl group on the nitrogen atom,
 b) from at least one acidic comonomer comprising at least one reactive carboxyl group, and
 c) from at least one basic comonomer such as esters with primary, secondary, tertiary and quaternary amine substituents of acrylic and methacrylic acids, and the product of quaternization of dimethylaminoethyl methacrylate with dimethyl or diethyl sulphate.

For instance, the N-substituted acrylamides or methacrylamides may be chosen from the compounds wherein the alkyl groups comprise from 2 to 12 carbon atoms, such as N-ethylacrylamide, N-tertbutylacrylamide, N-tertoctylacrylamide, N-octylacrylamide, N-decylacrylamide, N-dodecylacrylamide and the corresponding methacrylamides.

The acidic comonomers can be chosen from, for example, acrylic, methacrylic, crotonic, itaconic, maleic and fumaric acids and the 1-4 carbon alkyl monoesters of maleic or fumaric acids or anhydrides. The basic comonomers can be chosen from, for example, aminoethyl, butylaminoethyl, N,N'-dimethylamino-ethyl and N-tert. butylaminoethyl methacrylates. For instance, the copolymers whose CTFA name (4$^{th}$ Ed., 1991) is octylacrylamide/acrylates/butylaminoethyl methacrylate copolymer, such as the products sold by the company NATIONAL STARCH under the name AMPHOMER® or LOVOCRYL® 47 can be used.

(3) Crosslinked and acylated polyaminoamides partially or totally deriving from polyamino-amides of formula:

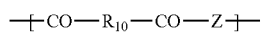

wherein $R_{10}$ is chosen from divalent groups derived from a saturated dicarboxylic acids, from mono and dicarboxylic aliphatic acids with ethylenic double bonds, from 1 to 6 carbon lower alkanol esters of these acids and from groups derived from the addition of any one of the acids with a bis-primary or bis-secondary amine, and Z is chosen from groups derived from bis-primary, mono and bis-secondary polyalkylene polyamines, such as, for example:

a) in an amount ranging from 60 mol % to 100 mol %, the group

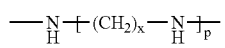

(III)

where x is equal to 2 and p is equal to 2 or 3, or else x is equal to 3 and p is equal to 2, this group deriving from diethylene-triamine, triethylene-tetraamine or dipropylene-triamine;

b) in an amount ranging from 0 mol % to 40 mol %, the group (III) above, wherein x is equal to 2 and p is equal to 1 and which derives from ethylene-diamine, or the group deriving from piperazine:

c) in an amount ranging from 0 mol % to 20 mol %, the group —NH—(CH$_2$)$_6$NH— deriving from hexamethylenediamine, these polyaminoamides being crosslinked by addition reaction of a bifunctional crosslinking agent selected from epihalohydrins, diepoxides, dianhydrides or bis-unsaturated derivatives, wherein there is from 0.025 to 0.35 moles of crosslinking agent per amine group of the polyamino-amide, and acylated by the action of acrylic acid, chloracetic acid or of an alkane sultone or salts thereof.

For example, the saturated carboxylic acids may be chosen from the acids comprising from 6 to 10 carbon atoms such as adipic, 2,2,4-trimethyladipic and 2,4,4-trimethyladipic and terephthalic acids and acids with ethylenic double bonds such as for example acrylic, methacrylic and itaconic acids.

The alkane sultones used in the acylation can be, for example, propane or butane-sultone, and the salts of these acylating agents may be, for instance, the sodium or potassium salts.

(4) Polymers comprising zwitterionic units of formula:

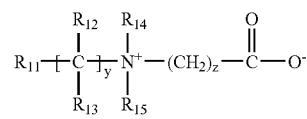

wherein $R_{11}$ is chosen from polymerizable unsaturated groups, such as an acrylate, methacrylate, acrylamide or methacrylamide group, y and z are integers from 1 to 3, $R_{12}$ and $R_{13}$ are chosen from hydrogen atoms, and methyl, ethyl and propyl groups, and $R_{14}$ and $R_{15}$ are chosen from hydrogen atoms and alkyl groups such that the sum of the carbon atoms in $R_{14}$ and $R_{15}$ does not exceed 10.

The polymers comprising such units can also comprise units derived from non-zwitterionic monomers such as dimethyl- or diethylaminoethyl acrylate or methacrylate or alkyl acrylates or methacrylates, acrylamides or methacrylamides, or vinyl acetate. By way of non-limiting example, the methyl methacrylate/methyl dimethylcarboxymethylammonioethyl methacrylate copolymers can be mentioned.

(5) Polymers derived from chitosan comprising monomer units of formulae:

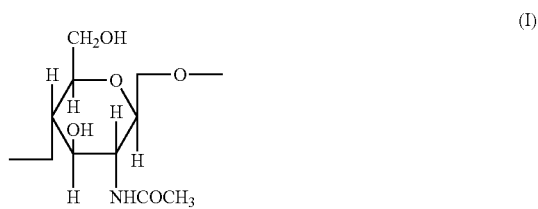

(I)

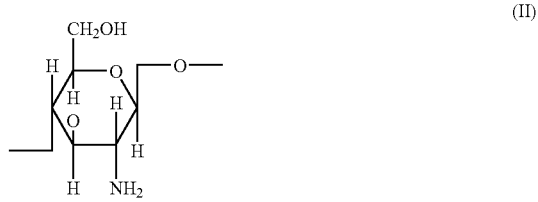

(II)

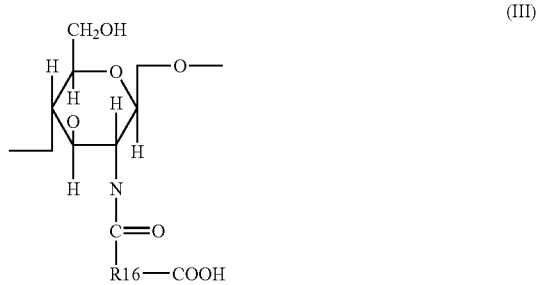

(III)

wherein the unit (I) is present in an amount ranging from 0% to 30%, the unit (II) is present in an amount ranging from 5% to 50% and the unit (III) is present in an amount ranging from 30% to 90%, it being understood that in this unit (III) $R_{16}$ is chosen from groups of formula:

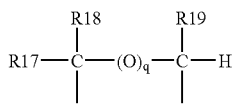

wherein if q is equal to 0, $R_{17}$, $R_{18}$ and $R_{19}$, which may be the same or different, are chosen from hydrogen atoms, methyl, hydroxy, acetoxy, and amino groups, and monoalkylamine and dialkylamine groups optionally interrupted by at least one nitrogen atom and/or optionally substituted with at least one entity chosen from amine, hydroxyl, carboxyl, alkylthio and sulphonic groups, and alkylthio groups wherein the alkyl group bears an amino group, wherein at least one of $R_{17}$, $R_{18}$ and $R_{19}$ in this case is a hydrogen atom; or if q is equal to 1, then $R_{17}$, $R_{18}$ and $R_{19}$ are hydrogen atoms, and also the salts formed by these compounds with bases or acids.

(6) Polymers of formula (V) which are, for example, described in French Patent No. 1,400,366:

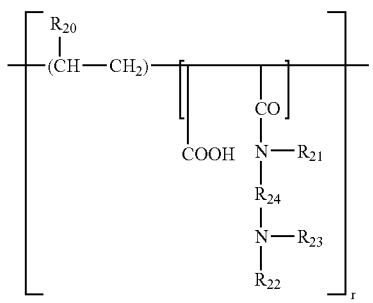

wherein $R_{20}$ is chosen from a hydrogen atom, and $CH_3O$, $CH_3CH_2O$ and phenyl groups, $R_{21}$ is chosen from a hydrogen atom, and lower alkyl groups, such as methyl or ethyl, $R_{22}$ is chosen from a hydrogen atom, and $C_1$-$C_6$ lower alkyl groups such as methyl or ethyl, $R_{23}$ is chosen from $C_1$-$C_6$ lower alkyl groups such as methyl or ethyl, and groups of formula —$R_{24}$—$N(R_{22})_2$—, wherein $R_{24}$ is chosen from —$CH_2$—$CH_2$—, —$CH_2$—$CH_2$—$CH_2$—and —$CH_2$—CH($CH_3$)—groups, wherein $R_{22}$ is chosen from a hydrogen atom, and $C_1$-$C_6$ lower alkyl groups such as methyl or ethyl, and wherein r is an integer greater than 1.

(7) Polymers derived from N-carboxyalkylation of chitosan such as N-carboxymethyl-chitosan or N-carboxybutyl-chitosan.

(8) Amphoteric polymers of the type D-X-D-X chosen from:
a) polymers obtained by the action of chloracetic acid or sodium chloracetate on compounds comprising at least one unit of formula (VI):

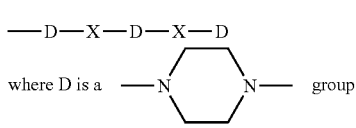

and X is chosen from E and E', wherein E and E', which may be the same or different, are bivalent groups chosen from straight and branched chain alkylene groups, comprising up to 7 carbon atoms in the main chain which can be unsubstituted or substituted with hydroxyl groups and can, in addition, comprise at least one atom chosen from oxygen, nitrogen and sulphur, and 1 to 3 aromatic and/or heterocyclic rings, wherein the atoms of oxygen, nitrogen and sulphur are present in the forms of ether, thioether, sulphoxide, sulphone, sulphonium, alkylamine, alkenylamine groups, benzylamine, amine oxide, quaternary ammonium, amide, imide, alcohol, ester and/or urethane groups.

b) polymers of formula (VI'):

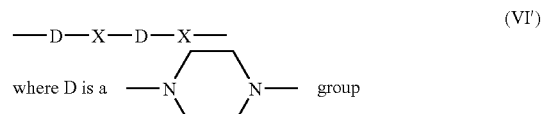

and X is chosen from E and E', and at least once E', wherein E has the meaning defined above and E' is a bivalent group chosen from straight and branched chain alkylene groups comprising up to 7 carbon atoms in the main chain, which is substituted or unsubstituted with at least one hydroxyl group, and comprises at least one nitrogen atom, wherein the nitrogen atoms are substituted with an alkyl chain optionally interrupted by an oxygen atom, and, in one embodiment, comprising at least one group chosen from carboxyl group and hydroxyl groups and betainised by reaction with chloracetic acid or sodium chloracetate.

(9) ($C_1$-$C_5$)alkyl vinyl ether/maleic anhydride copolymers partially modified by semi-amidation with an N,N-dialkylaminoalkylamine such as N,N-dimethylaminopropylamine or by semiesterification with an N,N-dialkylaminoalkanol. These copolymers can also comprise other vinyl comonomers such as vinylcaprolactam.

Among the amphoteric fixing polymers mentioned above, further non-limiting mention can be made of those of the family (3), such as the copolymers wherein the CTFA name is octylacrylamide/acrylates/butylamino-ethyl methacrylate copolymer, such as the products sold by the company NATIONAL STARCH under the names AMPHOMER®, AMPHOMER® LV 71 or LOVOCRYL® 47 and those of the family (4) such as the methyl methacrylate/methyl dimethyl-carboxymethyl-ammonio-ethyl methacrylate copolymers.

The nonionic fixing polymers usable according to the present disclosure can be chosen, for example, from:
polyalkyloxazolines;
homopolymers of vinyl acetate;
copolymers of vinyl acetate and acrylic ester;
copolymers of vinyl acetate and ethylene;
copolymers of vinyl acetate and a maleic ester, for example dibutyl maleate;
copolymers of acrylic esters such as, for example, the copolymers of alkyl acrylates and alkyl methacrylates such as the products offered by the company ROHM & HAAS under the names PRIMAL® AC-261 K and EUDRAGIT® NE 30 D, by the company BASF under the name 8845 and by the company HOECHST under the name APPRETAN® N9212;
copolymers of acrylonitrile and a nonionic monomer selected, for example, from butadiene and alkyl (meth) acrylates; the products offered by the company ROHM & HAAS under the name CJ 0601 B can be mentioned;
homopolymers of styrene;

copolymers of styrene and alkyl (meth)acrylate such as the products MOWILITH® LDM 6911, MOWILITH® DM 611 and MOWILITH® LDM 6070 offered by the company HOECHST, and the products RHODOPAS® SD 215 and RHODOPAS® DS 910 offered by the company RHODIA CHIMIE;

copolymers of styrene, alkyl methacrylate and alkyl acrylate;

copolymers of styrene and butadiene;

copolymers of styrene, butadiene and vinylpyridine;

copolymers of alkyl acrylate and urethane;

polyamides; and homopolymers and copolymers of vinyllactam.

The alkyl groups of the nonionic polymers mentioned above may have, for instance, from 1 to 6 carbon atoms.

According to the present disclosure, the nonionic fixing polymers with vinyllactam units can be those described in U.S. Pat. Nos. 3,770,683, 3,929,735, 4,521,504, 5,158,762 and 5,506,315 and in the International Patent Application Nos. WO 94/121148, WO 96/06592 and WO 96/10593. They can be in powder form or in solution or suspension form.

The homopolymers or copolymers with vinyllactam units comprise units of formula (IX):

(IX)

wherein n, which may be the same or different, is an integer chosen from 3, 4, or 5.

The number molecular weight of the polymers with vinyllactam units can be, for example, greater than 5,000, such as ranging from 10,000 to 1,000,000, for instance, ranging from 10,000 to 100,000.

Among these fixing polymers, non-limiting mention can be made of polyvinylpyrrolidones such as those marketed by the company BASF under the name Luviskol® K30, polyvinylcaprolactams such as those marketed by the company BASF under the name Luviskole PLUS, poly(vinylpyrrolidone/vinyl acetate) copolymers such as those marketed under the name PVPVA® S630L by the company ISP and Luviskol® VA 73, VA 64, VA 55, VA 37 and VA 28 by the company BASF, and poly(vinylpyrrolidone/vinyl acetate/vinyl propionate) terpolymers such as, for example those marketed by the company BASF under the name Luviskol® VAP 343.

The fixing polymers according to the present disclosure can also be chosen from nonionic and anionic, optionally siliconized, polyurethanes.

The at least one conditioning polymer and/or at least one fixing polymer can be present in an amount ranging from 0.01% to 20% by weight, relative to the weight of the dyeing composition, such as from 0.1% to 5% by weight, relative to the weight of the dyeing composition.

The composition may further comprise at least one additive chosen from surfactants, in turn chosen from nonionic, anionic, cationic, amphoteric and zwitterionic surfactants.

As non-limiting examples of anionic surfactants that may be used alone or as mixtures, the salts of the following compounds may be mentioned, such as the salts of alkali or alkaline earth metals, for instance sodium and magnesium, ammonium salts, amine salts and amino alcohol salts; the alkylsulphates, alkylethersulphates, alkylamidoethersulphates, alkylarylpolyethersulphates, sulphate monoglycerides, alkylsulphonates, alkylphosphates, alkylamide-sulphonates, alkylarylsulphonates, α-olefinsulphonates, paraffinsulphonates, ($C_6$-$C_{24}$) alkyl-sulphosuccinates, ($C_6$-$C_{24}$) alkylethersulphosuccinates, ($C_6$-$C_{24}$) alkylamidesulphosuccinates, ($C_6$-$C_{24}$) alkylsulphoacetates, ($C_6$-$C_{24}$) acylsarcosinates and ($C_6$-$C_{24}$) acylglutamates.

The carboxylic esters of ($C_6$-$C_{24}$) alkylpolyglycosides such as alkylglucoside citrates, alkylpolyglycoside tartrates and alkylpolyglycoside sulphosuccinates, alkylsulphosuccinamates, acylisethionates and N-acyltaurates can also be used. For example, the alkyl or acyl group of the previously mentioned compounds may be from $C_{12}$-$C_{20}$, and the aryl group may be chosen from phenyl and benzyl groups.

Among the anionic surfactants that may also be used, the salts of fatty acids such as the salts of oleic, ricinoleic, palmitic and stearic acids, copra oil or hydrogenated copra oil acids, and acyl-lactylates wherein the acyl group is $C_8$-$C_{20}$, can also be mentioned in a non-limiting manner.

Further non-limiting mention can be made of the alkyl D galactoside uronic acids and salts thereof, polyoxyalkylenated ($C_6$-$C_{24}$) alkylethercarboxylic acids, polyoxyalkylenated (C6-$C_{24}$) alkylarylethercarboxylic acids, polyoxyalkylenated ($C_6$-$C_{24}$) alkylamidoether carboxylic acids and salts thereof, such as those comprising from 2 to 50 alkylene, for instance ethylene, oxide groups, and mixtures thereof.

As non-limiting examples of nonionic surfactants, among others, polyethoxylated and/or polypropoxylated $C_8$-$C_{18}$ alcohols, alpha diols and alkylphenols, the number of ethylene oxide and/or propylene oxide groups ranging from 2 to 50, may be mentioned.

Further non-limiting mention can be made of copolymers of ethylene oxide and propylene oxide, condensates of ethylene oxide and propylene oxide with fatty alcohols, polyethoxylated fatty amides for example comprising from 2 to 30 moles of ethylene oxide, polyglycerolated fatty amides comprising on average 1 to 5 and such as 1.5 to 4 glycerol groups, polyethoxylated fatty amines for example, comprising from 2 to 30 moles of ethylene oxide, oxyethylenated fatty acid esters of sorbitan comprising from 2 to 30 moles of ethylene oxide, fatty acid esters of sucrose, fatty acid esters of polyethylene glycol, alkyl-polyglycosides, N-alkylglucamine derivatives, amine oxides such as the oxides of ($C_{10}$-$C_{14}$) alkylamines or N-acylaminopropylmorpholine oxides.

With regard to the amphoteric or zwitterionic surfactants, non-limiting mention can be made of the derivatives of secondary or tertiary aliphatic amines, wherein the aliphatic group is a linear or branched chain comprising from 8 to 18 carbon atoms and comprising at least one water-solubilising anionic group (for example carboxylate, sulphonate, sulphate, phosphate or phosphonate); the ($C_8$-$C_{20}$) alkylbetaines, the sulphobetaines, the ($C_8$-$C_{20}$) alkylamido ($C_1$-$C_6$) alkylbetaines or the ($C_8$-$C_{20}$) alkylamido ($C_1$-$C_6$) alkylsulphobetaines can also be mentioned in a non-limiting manner.

Among the amine derivatives that may be used as disclosed herein, non-limiting examples include the products sold under the name MIRANOL, such as described in U.S. Pat. Nos. 2,528,378 and 2,781,354 and classified in the CTFA dictionary, 3$^{rd}$ edition, 1982, under the names amphocarboxyglycinates and amphocarboxy-propionates of respective structures:

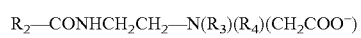

wherein:

$R_2$ is chosen from alkyl groups of an acid $R_2$—COOH present in hydrolysed copra oil, and heptyl, nonyl and undecyl groups, $R_3$ is a beta-hydroxyethyl group and $R_4$ is a carboxymethyl group, and

$R_2'$—CONHCH$_2$CH$_2$—N(B)(C)

wherein:

B is the group —CH$_2$CH$_2$OX', C is chosen from —(CH$_2$)$_z$—Y' groups, with z equal to 1 or 2, X' is chosen from —CH$_2$CH$_2$—COOH groups and a hydrogen atom Y' is chosen from —COOH and —CH$_2$—CHOH—SO$_3$H groups $R_2'$ is chosen from alkyl groups of an acid $R_2$—COOH present in copra oil or in hydrolysed linseed oil, alkyl groups, such as $C_7$, $C_9$, $C_{11}$ and $C_{13}$, $C_{17}$ alkyl groups and their iso form and unsaturated $C_{17}$ groups.

These compounds are classified in the CTFA dictionary, 5$^{th}$ edition, 1993, under the names disodium cocoamphodiacetate, disodium lauroamphodiacetate, disodium caprylamphodiacetate, disodium capryloamphodiacetate, disodium cocoamphodipropionate, disodium lauroamphodipropionate, disodium caprylamphodipropionate, disodium caryloampho-dipropionate, lauroamphodipropionic acid, cocoamphodipropionic acid and disodium cocoamphocarboxy ethyl hydroxypropyl sulphonate.

As non-limiting examples, the cocoamphodiacetate marketed by the company Rhodia Chimie under the trade name concentrated MIRANOL® C2M can be mentioned.

Among the cationic surfactants, non-limiting mention can be made of, for instance the salts of primary, secondary or tertiary fatty amines, optionally polyoxyalkylenated, quaternary ammonium salts such as tetraalkylammonium, alkylamidoalkyltrialkylammonium, trialkylbenzylammonium, trialkyl-hydroxyalkylammonium or alkylpyridinium chlorides or bromides, imidazoline derivatives, or amine oxides of cationic nature, or the quaternary mono- and di-esters called ester quat.

The at least one surfactant, when present, can be present in an amount, for example, ranging from 0.001% to 30% by weight, such as from 0.05 to 30% by weight, relative to the weight of the dyeing composition.

The dyeing composition can further comprise at least one additional direct dye different from the compound of formula (I), chosen from nonionic and ionic dyes, such as nonionic and cationic species.

For example, the at least one additional direct dye can be chosen from the acridine, acridone, anthranthrone, anthrapyrimidine, anthraquinone, azine, azo, azomethine, benzanthrone, benzimidazole, benzimidazolone, benzindole, benzoxazole, benzopyran, benzothiazole, benzoquinone, bisazine, bis isoindoline, carboxanilide, coumarin, cyanine such as azacarbocyanine, diazacarbocyanine, diazahemicyanine, hemicyanine and tetraazacarbocyanine), diazine, diketopyrrolopyrrole, dioxazine, diphenylamine, diphenylmethane, dithiazine, flavanthrone, flavone, fluorindine, formazan, hydrazone, hydroxyketone, indamine, indanthrone, indigoid, indophenol, indoaniline, isoindoline, isoindolinone, isoviolanthrone, lactone, methine, naphthalimide, naphthanilide, naphtholactam, naphthoquinone, nitro, oxadiazole, oxazine, perilone, perinone, perylene, phenazine, phenothiazine, phthalocyanine, polyene/carotenoid, porphyrin, pyranthrone, pyrazolanthrone, pyrazolone, pyrimidinoanthrone, pyronine, quinacridone, quinoline, quinophthalone, squarane, stilbene, tetrazolium, thiazine, thioindigo, thiopyronine, triarylmethane and xanthene dyes, alone, or in mixtures.

If present in the dyeing composition, the at least one additional direct dye different from the compounds of formula (I) can be present in an amount ranging from 0.0005% to 12% by weight, relative to the weight of the dyeing composition, such as from 0.005% to 6% by weight, relative to the weight of the dyeing composition.

In another aspect of the present disclosure, the dyeing composition used can also comprise at least one oxidation base, if desired, together with at least one coupler.

The at least one oxidation base can be chosen from the typical compounds in the field of dyeing. As non-limiting examples, among others o-phenylenediamines, p-phenylenediamines, double bases, o-aminophenols, p-aminophenols, heterocyclic bases, addition salts thereof with an acid, and mixtures thereof can be mentioned.

If present, the at least one oxidation base can be present in an amount ranging from 0.0005% to 12% by weight, relative to the weight of the composition, such as from 0.005% to 8% by weight, relative to the weight of the composition.

Among the couplers usable together with at least one oxidation base, non-limiting mention can be made of, for example, the m-aminophenols, m-phenylenediamines, m-diphenols, naphthols, heterocyclic couplers, addition salts thereof with an acid, and mixtures thereof.

If present in the dyeing composition, the at least one coupler can be present in an amount ranging from 0.0001% to 10% by weight, relative to the weight of the composition, such as from 0.005% to 5% by weight, relative to the weight of the composition.

In general, the addition salts of the oxidation bases and couplers with an acid can be, for example, selected from the hydrochlorides, hydrobromides, sulphates and the tartrates, lactates and acetates.

The composition according to the present disclosure can also comprise at least one typically used additive, such as inorganic thickeners, antioxidants, penetration agents, perfumes, buffers, dispersing agents, ester type agents, oils and vegetable waxes, mineral oils, film-forming agents, ceramides, vitamins or provitamins, preservatives, stabilisers, opacifiers or matting agents such as titanium oxide, inorganic fillers such as clays, silicas, for instance, calcined and of a hydrophilic or hydrophobic nature, binding polymers such as vinylpyrrolidone, sun filters, and the like.

The at least one additive can be present, for example, in an amount ranging from 0.01% to 20% by weight, relative to the weight of the composition.

The medium of the dyeing composition is a cosmetically acceptable medium. For example, the medium can be made up of water or a mixture of water and at least one organic solvent.

Among the usual organic solvents, non-limiting mention can be made of, for example, the linear or branched monoalcohols or diols, for instance, saturated, comprising from 2 to 10 carbon atoms, such as ethyl alcohol, isopropyl alcohol, hexylene glycol (2-methylpentane-2,4-diol), neopentyl glycol and 3-methylpentane-1,5-diol, aromatic alcohols such as benzyl alcohol and phenylethyl alcohol, glycols or glycol ethers such as for example the monomethyl, monoethyl and monobutyl ethers of ethylene glycol, propylene glycol or ethers thereof such as, for example, the monomethyl ether of propylene glycol, butylene glycol and dipropylene glycol, and also the alkyl, for instance, $C_1$-$C_4$, ethers of diethylene glycol such as, for example, the monoethyl ether or the monobutyl ether of diethylene glycol, alone or as mixtures.

When present, the at least one organic solvent can be present, in an amount ranging from 1% to 40% by weight, such as from 5% to 30% by weight, relative to the total weight of the composition.

The composition as disclosed herein can be in the form of a lotion, thickened or otherwise, a cream, a gel, or any other form appropriate for the subsequent use of this composition.

In another aspect of the present disclosure, the dyeing composition can, if desired, further comprise at least one oxidizing agent. If the composition as disclosed herein comprises at least one oxidizing agent, then this composition, also referred to as ready-to-use composition, for example, results from the mixing of the previously described composition devoid of oxidizing agent with a composition comprising at least one oxidizing agent (that composition can then be referred to as the oxidizing composition). In this case, the mixing is effected before the application of the ready-to-use composition onto the fibers to be treated.

For example, the at least one oxidizing agent can be chosen from hydrogen peroxide, peroxides of alkali or alkaline earth metals, such as sodium, potassium and magnesium, urea peroxide, bromates or ferricyanides of alkali metals, persalts such as the perborates and persulphates of alkali or alkaline earth metals, such as sodium, potassium or magnesium, alone or as mixtures. The oxidizing agent can also be chosen from enzymes such as the peroxidases and two- or four-electron oxidoreductases. In one embodiment of the present disclosure, the at least one oxidizing agent is hydrogen peroxide.

If it is present, the at least one oxidizing agent can be present in an amount ranging from 0.001% to 20% by weight, relative to the weight of the ready-to-use dyeing composition.

The medium of the oxidising composition can be, for example, water or a mixture of water and at least one organic solvent.

The oxidizing composition can comprise at least one usual additive in the field, such as surfactants, thickeners, antioxidants, perfumes, dispersants, conditioning agents, sequestering agents, preservatives, and the like. For clarity, it is stated that the lists of solvents and additives, and likewise their contents, indicated in the context of the description of the dyeing composition remain valid, and reference can be made to them.

The pH of the dyeing composition used in the process according to the present disclosure ranges from 5 to 11, such as from 6 to 8.5. It can be adjusted to the desired value by means of acidification or basification agents.

Among the acidification agents, inorganic or organic acids such as hydrochloric acid, orthophosphoric acid, sulphuric acid and acetic acid can be mentioned as non-limiting examples.

Among the basification agents, ammonia, alkali metal carbonates, alkanolamines such as mono-, di- and triethanolamines and derivatives thereof, sodium or potassium hydroxides and the compounds of formula (A) can be mentioned as non-limiting examples:

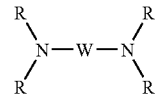

(A)

wherein W is chosen from propylene groups optionally substituted with a hydroxyl group or a $C_1$-$C_6$ alkyl group, and R, which may be the same or different, can be chosen from hydrogen atoms, $C_1$-$C_6$ alkyl and $C_1$-$C_6$ hydroxyalkyl groups.

In one aspect of the present disclosure, the process as disclosed herein comprises applying to the fibers, dry or moist, a composition comprising at least one compound of formula (I), for a period sufficient for the development of the coloration, optionally rinsing the fibers, optionally washing and rinsing the fibers, and drying or allowing the fibers to air dry.

According to another aspect of the process, the composition applied onto the fibers does not comprise an oxidising agent. This aspect is appropriate when the composition comprises only the compound or compounds of formula (I) and optionally, at least one additional direct dye. In the context of this aspect, it is conceivable not to rinse the fibers once treated nor to wash them with shampoo. However, for example, it may be desired that such a rinsing will be performed, and possibly a washing of the fibers with a shampoo.

According to yet another aspect of the process, the composition applied onto the fibers is a composition comprising at least one oxidising agent. This aspect of the process is appropriate for any dyeing composition used, i.e., both when the dye composition only comprises at least one compound of formula (I) and optionally at least one additional direct dye, and if it comprises, in addition to the at least one compound of formula (I), at least one oxidation base and optionally at least one coupler. According to this aspect, a first possibility comprises in the application of the composition obtained by mixing of the dyeing composition devoid of oxidizing agent with an oxidizing composition on the spot before application to the fibers. According to this option, it may be desired, for example, to stock on the one hand the dyeing composition devoid of oxidizing agent, and on the other hand an oxidizing composition in separate form.

A second option comprises in successively applying the dyeing composition devoid of oxidizing agent and of the oxidizing composition to the fibers, in one order or the other, and with or without intermediate rinsing, or else comprises the application of both these compositions simultaneously to the fibers. In this second option, once both compositions have been added and the leave-in time, if any, has ended, the fibers can optionally be rinsed), and optionally be washed with a shampoo. In one embodiment of the present disclosure, the fibers are washed and rinsed.

The fibers can then be dried or else allowed to dry, for example at a temperature ranging from 20° C. and 220° C.

The period of leave-in time for the development of the coloration can range, for example, from 1 to 60 minutes, such as from 5 to 45 minutes.

Moreover, the at least one composition can be applied to the fibers at a temperature ranging from 15° C. to 220° C., such as from 15° C. and 40° C.

Other than in the operating examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the invention are approximations, the numerical values set forth in the specific example are reported as precisely as possible. Any numerical value, however, inherently contain certain errors necessarily resulting from the standard deviation found in their respective testing measurements.

The following examples are intended to illustrate the invention in a non-limiting manner.

EXAMPLES 1 TO 4

Example 1

The following dyeing composition 1 was prepared:

| Constituent | Amount |
|---|---|
| 7,14-bis-(2-hydroxyethyl)-5-methyl-7,14-dihydroquinoxalino-[2,3-b]phenazin-5-ium chloride ($1^{-3}$ moles) (*) | 0.39 g |
| Benzyl alcohol | 4.0 g |
| Polyethylene glycol 6 EO | 6.0 g |
| Hydroxyethylcellulose | 0.7 g |
| Alkylpolyglucoside in aqueous solution with 60% A.S. ** | 4.5 g A.S. |
| Phosphate buffer | q.s. for pH 7 |
| Demineralised water | q.s.p 100 g |

\* compound of the following formula:

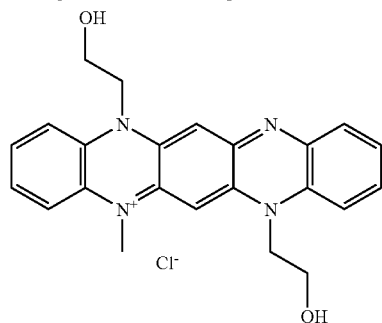

\*\* Active Substance

The above composition was applied to locks of natural grey or permed grey hair with 90% white hair and allowed to stand for 20 minutes.

After rinsing in running water and drying, the hair had been dyed a blue shade.

Example 2

The following dyeing composition 2 was prepared:

| Constituent | Amount |
|---|---|
| 1H-Benzo[ij]quinolizinium chloride, 9-[bis(2,3,6,7-tetrahydro-1H,5H-benzo[ij]quinolizin-9-yl)methylene]-2,3,5,6,7,9-hexahydro ($10^{-3}$ moles) (*) | 0.39 g |
| Oleic diethanolamide | 3 g |
| Lauric acid | 1 g |
| Ethylene glycol monoethyl ether | 5 g |
| Hydroxyethylcellulose | 2 g |
| 2-amino-2-methylpropan-1-ol | q.s. for pH 9.5 |
| Demineralised water | q.s.p 100 g |

The above composition was applied to locks of natural grey or permed grey hair with 90% white hair and allowed to stand for 30 minutes.

After rinsing in running water and drying, the hair had been dyed a blue shade.

Examples 3(A) to 3(D)

The following compositions 3(A) to 3(D), which are in accordance with the present disclosure, were prepared (contents in grams):

| | COMPOSITION | | | |
|---|---|---|---|---|
| | A | B | C | D |
| Paratoluylenediamine | 0.25 | — | — | — |
| Para-aminophenol | 0.30 | 0.50 | 0.15 | — |
| Paraphenylenediamine | — | 0.20 | — | 0.30 |
| 5-N-(β-hydroxyethyl)amino 2-methyl phenol | 0.5 | 0.8 | 0.17 | — |
| 5-amino 2-methyl phenol | — | — | — | 0.30 |
| Cationic dye of structure (1) | 0.39 | 0.39 | 0.39 | 0.39 |
| Common dye support (*) | (*) | (*) | (*) | (*) |
| Water q.s.p. | 100 g | 100 g | 100 g | 100 g |

(*) common dye support:

| | |
|---|---|
| Oleyl alcohol polyglycerolated with 2 moles of glycerol | 4.0 g |
| Oleyl alcohol polyglycerolated with 4 moles of glycerol, with 78% active substances (A.S.) | 5.69 g A.S. |
| Oleic acid | 3.0 g |
| Oleic acid with 2 moles of ethylene oxide sold by the company AKZO under the trade name ETHOMEEN O12 | 7.0 g |
| Diethylaminopropyl laurylaminosuccinate, sodium salt, with 55% A.S. | 3.0 g A.S. |
| Oleyl alcohol | 5.0 g |
| Oleic acid diethanolamide | 12.0 g |
| Propylene glycol | 3.5 g |
| Ethyl alcohol | 7.0 g |
| Dipropylene glycol | 0.5 g |
| Propylene glycol monomethyl ether | 9.0 g |
| Sodium metabisulphite in aqueous solution, with 35% A.S. | 0.455 g A.S. |
| Ammonium acetate | 0.8 g |
| Antioxidant, sequestering agent | q.s. |
| Perfume, preservative | q.s. |
| Aq. ammonia with 20% $NH_3$ | 10.0 g |

At the time of use, each of the compositions 3(A) to 3(D) was mixed with an equal quantity of a composition (X) coomprising a 20 volumes hydrogen peroxide solution (6% by weight).

Each resulting composition (ready-to-use composition in accordance with present disclosure) was applied for 30 minutes onto locks of natural grey hair with 90% white.

The locks of hair were then rinsed, washed with a standard shampoo then dried.

The locks of hair had been dyed in the shades shown in the table below:

| EXAMPLE | SHADE OBTAINED |
|---|---|
| COMPOSITION A | Dark blonde with blue highlight |
| COMPOSITION B | Blonde with blue highlight |
| COMPOSITION C | Light blonde with blue highlight |
| COMPOSITION D | Blonde with blue highlight |

The shades obtained displayed very good fastness to subsequent shampoo washings.

Examples 4 and 4'

The following composition 4 was prepared:

| Composition 4 | |
|---|---|
| 1,4-diamino benzene | 0.40 g |
| 5-amino 2-methyl phenol | 0.45 g |
| common dye support as described above for example 3 | (*) |
| demineralised water q.s.p. | 100 g |

The following composition 4' was prepared:

| Composition 4' | |
|---|---|
| cationic dye 7,14-bis-(2-hydroxyethyl)-5-methyl-7,14-dihydro-quinoxalino[2,3-b]phenazin-5-ium chloride | 4 g |
| quaternary polyammonium sold by the company National Starch under the trade name CELQUAT SC-240 | 10 g |
| wood sawdust q.s.p. | 100 g |

At the time of use, one part by weight of the above composition 4 was mixed with 0.1 parts by weight of the composition 4' and with one part by weight of a composition (X) comprising 20 volumes of a hydrogen peroxide solution (6% by weight).

The resulting composition was applied to locks of natural grey or permed grey hair with 90% white hair for 30 minutes. The hair was then rinsed, washed with a standard shampoo, then dried.

The hair had been dyed in a light brown shade with blue highlight which withstood subsequent shampoo washings very well.

What is claimed is:

1. A process for the dyeing of keratinic fibers, comprising applying to wet or dry fibers, for a period of time sufficient for the development of color, a dyeing composition comprising as a direct dye, in a medium appropriate for the dyeing of keratin fibers, at least one compound of formula (I):

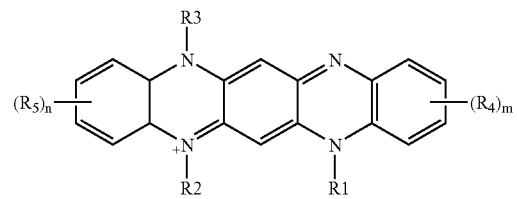

wherein:

$R_1$, $R_2$ and $R_3$, which may be the same or different, are chosen from linear and branched $C_1$-$C_{24}$ alkyl groups, $C_6$-$C_{30}$ aryl groups, and aralkyl groups wherein the aryl part is $C_6$-$C_{30}$ and the linear or branched alkyl part is $C_1$-$C_{24}$;

$R_4$ and $R_5$, which may be the same or different, are chosen from hydrogen atoms, halogen atoms, hydroxy groups, linear and branched $C_1$-$C_{24}$ alkyl groups, linear and branched $C_1$-$C_{24}$ alkoxy groups, monohydroxy alkoxy groups, wherein the alkyl part is linear or branched $C_1$-$C_6$, polyhydroxy alkoxy groups wherein the alkyl part is linear or branched $C_1$-$C_6$, amino groups optionally substituted with at least one group chosen from linear and branched $C_1$-$C_6$ alkyl groups, which may be the same or different, optionally substituted with at least one hydroxyl group, thiol groups, alkylthio groups wherein the alkyl part is linear or branched $C_1$-$C_6$, carboxyl groups in acid or salt form, with an alkali metal or substituted or unsubstituted ammonium, alkoxycarbonyl groups wherein the alkyl part is linear or branched $C_1$-$C_6$, alkylamide groups wherein the alkyl part is linear or branched $C_1$-$C_6$, alkylcarbamyl groups wherein the alkyl part is linear or branched $C_1$-$C_6$, alkyl part is linear or branched $C_1$-$C_6$, alkylsulphonylamido groups wherein the alkyl part is linear or branched $C_1$-$C_6$, $C_6$-$C_{30}$ aryl groups optionally substituted with at least one $C_1$-$C_6$ alkyl group, and aralkyl groups wherein the aryl part is $C_6$-$C_{30}$, optionally substituted with at least one $C_1$-$C_6$ alkyl group, and the linear or branched alkyl part is $C_1$-$C_{24}$, wherein the alkyl and aryl groups and/or parts, are optionally substituted with at least one entity chosen from hydroxyl groups, —$SO_3^-$ groups, —$COO^-$ groups, halogen atoms, $C_1$-$C_6$ alkoxy groups, monohydroxy alkoxy groups wherein the alkyl part is linear or branched $C_1$-$C_6$, polyhydroxy alkoxy groups wherein the alkyl part is linear or branched $C_1$-$C_6$, amino groups optionally substituted with at least one group chosen from linear and branched $C_1$-$C_6$ alkyl groups, which may be the same or different, optionally substituted with at least one hydroxyl group, n and m, which may be the same or different, are integers ranging from 0 to 4, An is at least one anion that is cosmetically acceptable; and p is equal to 0 or 1, so as to respect the electroneutrality of the compound; and optionally rinsing the fibers, optionally washing and rinsing the fibers, and optionally drying or allowing the fibers to dry.

2. The process according to claim 1, wherein $R_1$, $R_2$ and $R_3$, which may be the same or different, are chosen from $C_1$-$C_6$ alkyl groups, phenyl groups, aralkyl groups wherein the aryl part is $C_6$ and the alkyl part is $C_1$-$C_6$, wherein the alkyl, phenyl and aralkyl groups are optionally substituted with at least one entity chosen from the hydroxyl groups, —$SO_3^-$ groups, —$COO^-$ groups, halogen atoms, $C_1$-$C_6$ alkoxy groups, amino groups, (di)alkylamino groups wherein the alkyl part is $C_1$-$C_6$ and (di)hydroxyalkylamino groups wherein the alkyl part is $C_1$-$C_6$.

3. The process according to claim 2, $R_1$, $R_2$ and $R_3$, which may be the same or different, are chosen from methyl, ethyl, methoxy, hydroxyethyl, phenyl and 3-sulphopropyl groups.

4. The process according to claim 1, wherein $R_4$ and $R_5$, which may be the same or different, are chosen from hydrogen atoms, chlorine atoms, amino groups, (di)alkylamino groups wherein the alkyl part is $C_1$-$C_6$, (di)hydroxyalkylamino groups wherein the alkyl part is $C_1$-$C_6$, hydroxy groups, linear and branched $C_1$-$C_6$ alkyl groups, and linear and branched $C_1$-$C_6$ alkoxy groups,
  wherein the alkyl or alkoxy groups are optionally substituted with at least one entity chosen from hydroxy groups, halogen groups, $C_1$-$C_6$ alkoxy groups, amino groups, (di)alkylamino groups wherein the alkyl part is $C_1$-$C_6$, and (di)hydroxyalkylamino groups wherein the alkyl part is $C_1$-$C_6$.

5. The process according to claim 4, wherein $R_4$ and $R_5$, which may be the same or different, are chosen from hydrogen atoms, methyl groups, ethyl groups, methoxy groups, ethoxy groups, hydroxy groups, amino groups, dimethylamino groups, dihydroxyethylamino groups, and chlorine atoms.

6. The process according to claim 1, wherein the at least one compound of formula (I) is present in an amount ranging from 0.001% to 20% by weight, relative to the weight of the dyeing composition.

7. The process according to claim 1, wherein the dyeing composition comprises at least one additional direct dye different from the compound of formula (I), chosen from nonionic and ionic species.

8. The process according to claim 7, wherein the at least one additional direct dye is chosen from acridine, acridone, anthranthrone, anthrapyrimidine, anthraquinone, azine, azo, azomethine, benzanthrone, benzimidazole, benzimidazolone, benzindole, benzoxazole, benzopyran, benzothiazole, benzoquinone, bisazine, bis isoindoline, carboxanilide, coumarin, cyanine, diazine, diketopyrrolopyrrole, dioxazine, diphenylamine, diphenylmethane, dithiazine, flavanthrone, flavone, fluorindine, formazan, hydrazone, hydroxyketone, indamine, indanthrone, indigoid, indophenol, indoaniline, isoindoline, isoindolinone, isoviolanthrone, lactone, methine, naphthalimide, naphthanilide, naphtholactam, naphthoquinone, nitro, oxadiazole, oxazine, perilone, perinone, perylene, phenazine, phenothiazine, phthalocyanine, polyene/carotenoid, porphyrin, pyranthrone, pyrazolanthrone, pyrazolone, pyrimidinoanthrone, pyronine, quinacridone, quinoline, quinophthalone, squarane, stilbene, tetrazolium, thiazine, thioindigo, thiopyronine, triarylmethane and xanthene dyes.

9. The process according to claim 8, wherein the at least one additional direct dye different from the compounds of formula (I) is present in an amount ranging from 0.0005% to 12% by weight, relative to the weight of the dyeing composition.

10. The process according to claim 1, wherein the dyeing composition further comprises at least one oxidizing agent.

11. The process according to claim 10, wherein the at least one oxidizing agent is chosen from hydrogen peroxide, urea peroxide, bromates and ferricyanides of alkali metals, persalts, and enzymes.

12. The process according to claim 10, wherein the dyeing composition further comprises at least one additive chosen from oxidation bases and couplers.

13. A dyeing composition comprising, as a direct dye, in a medium appropriate for the dyeing of keratinic fibers, at least one compound of formula (I):

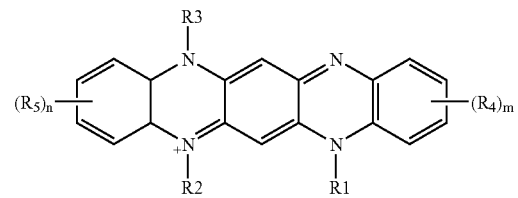

wherein:
  $R_1$, $R_2$ and $R_3$, which may be the same or different, are chosen from linear and branched $C_1$-$C_{24}$ alkyl groups, $C_6$-$C_{30}$ aryl groups, and aralkyl groups wherein the aryl part is $C_6$-$C_{30}$ and the linear or branched alkyl part is $C_1$-$C_{24}$;
  $R_4$ and $R_5$, which may be the same or different, are chosen from hydrogen atoms, halogen atoms, hydroxy groups, linear and branched $C_1$-$C_{24}$ alkyl groups, linear and branched $C_1$-$C_{24}$ alkoxy groups, monohydroxy alkoxy groups wherein the alkyl part is linear or branched $C_1$-$C_6$, polyhydroxy alkoxy groups wherein the alkyl part is linear or branched $C_1$-$C_6$, amino groups optionally substituted with at least one group chosen from linear and branched $C_1$-$C_6$ alkyl groups, which may be the same or different, are optionally substituted with at least one hydroxyl group, thiol groups, alkylthio groups wherein the alkyl part is linear or branched $C_1$-$C_6$, carboxyl groups in acid or salt form, with an alkali metal or substituted or unsubstituted ammonium, alkoxycarbonyl groups wherein the alkyl part is linear or branched $C_1$-$C_6$, alkylamide groups wherein the alkyl part is linear or branched $C_1$-$C_6$, alkylcarbamyl groups wherein the alkyl part is linear or branched $C_1$-$C_6$, cyano groups, nitro groups, sulphonyl groups, alkylsuiphonyl groups wherein the alkyl part is linear or branched $C_1$-$C_6$, alkylsulphonylamido groups wherein the alkyl part is linear or branched $C_1$-$C_6$, $C_6$-$C_{30}$ aryl groups optionally substituted with at least one $C_1$-$C_6$ alkyl group, and aralkyl groups wherein the aryl part is $C_6$-$C_{30}$, optionally substituted with at least one $C_1$-$C_6$ alkyl groups, and the linear or branched alkyl part is $C_1$-$C_{24}$,
    wherein the alkyl and aryl groups and/or parts are optionally substituted with at least one entity chosen from hydroxyl groups, —$SO_3^-$ groups, —$COO^-$ groups, halogen atoms, $C_1$-$C_6$ alkoxy groups, monohydroxy alkoxy groups wherein the alkyl part is linear or branched $C_1$-$C_6$, polyhydroxy alkoxy groups wherein the alkyl part is linear or branched $C_1$-$C_6$, and amino groups optionally substituted with at least one group chosen from linear and branched $C_1$-$C_6$ alkyl groups, which may be the same or different, optionally substituted with at least one hydroxyl group,
  n and m, which may be the same or different, are integers ranging from 0 to 4,
  An is at least one anion that is cosmetically acceptable; and p is equal to 0 or 1, so as to respect the electroneutrality of the compound; and at least one additive chosen from polymers.

14. The dyeing composition according to claim 13, wherein $R_1$, $R_2$ and $R_3$, which may be the same or different, are chosen from $C_1$-$C_6$ alkyl groups, phenyl groups, aralkyl groups, wherein the aryl part is $C_6$ and the alkyl part is $C_1$-$C_6$, wherein the alkyl, phenyl and aralkyl groups are optionally substituted with at least one entity chosen from hydroxy groups, halogen atoms, $C_1$-$C_6$ alkoxy groups, amino groups, (di)alkylamino groups, wherein the alkyl part is $C_1$-$C_6$, and (di)hydroxyalkylamino groups, wherein the alkyl part is $C_1$-$C_6$.

15. The dyeing composition according to claim 14, $R_1$, $R_2$ and $R_3$, which may be the same or different, are chosen from methyl, ethyl, methoxy, hydroxyethyl, phenyl and 3-sulphopropyl groups.

16. The dyeing composition according to claim 13, wherein $R_4$ and $R_5$, which may be the same or different, are chosen from hydrogen atoms, chlorine atoms, amino groups, (di)alkylamino groups, wherein the alkyl part is $C_1$-$C_6$, (di)hydroxyalkylamino groups, wherein the alkyl part is $C_1$-$C_6$, hydroxy groups, linear and branched $C_1$-$C_6$ alkyl groups, and linear and branched $C_1$-$C_6$ alkoxy groups, wherein the said alkyl and alkoxy groups are optionally substituted with at least one entity chosen from hydroxy groups, halogen atoms, $C_1$-$C_6$ alkoxy groups, amino groups, (di)alkylamino groups, wherein the alkyl part is $C_1$-$C_6$, and (di)hydroxyalkylamino groups wherein the alkyl part is $C_1$-$C_6$.

17. The dyeing composition according to claim 16, wherein $R_4$ and $R_5$, which may be the same or different, are chosen from hydrogen atoms, methyl groups, ethyl groups, methoxy groups, ethoxy groups, hydroxy groups, amino groups, dimethylamino groups, dihydroxyethylamino groups, and chlorine atoms.

18. The dyeing composition according to claim 13, wherein the at least one compound of formula (I) is present in an amount ranging from 0.001% to 20% by weight, relative to the weight of the dyeing composition.

19. The dyeing composition according to claim 13, the at least one polymer is chosen from nonionic, anionic, cationic and amphoteric polymers.

20. The dyeing composition according to claim 13, wherein the at least one polymer is chosen from nonionic, cationic, anionic and amphoteric surfactants.

21. The dyeing composition according to claim 20, wherein the at least one surfactant is present in an amount ranging from 0.001 to 30% by weight, relative to the weight of the dyeing composition.

22. The dyeing composition according claim 13, wherein the at least one polymer is chosen from associative and non-associative thickening polymers.

23. The dyeing composition according to claim 22, wherein the at least one associative and/or at least one non-associative thickening polymer is present in an amount ranging from 0.01% to 10% by weight, relative to the weight of the dyeing composition.

24. The dyeing composition according to claim 13, wherein the at least one polymer is chosen from conditioning polymers and fixing polymers.

25. The dyeing composition according to claim 24, wherein the at least one conditioning polymer and/or fixing polymer is present in an amount ranging from 0.01% to 20% by weight, relative to the weight of the dyeing composition.

* * * * *

UNITED STATES PATENT AND TRADEMARK OFFICE
CERTIFICATE OF CORRECTION

| | | |
|---|---|---|
| PATENT NO. | : 7,294,152 B2 | |
| APPLICATION NO. | : 11/030170 | |
| DATED | : November 13, 2007 | |
| INVENTOR(S) | : Alain Lagrange | |

It is certified that error appears in the above-identified patent and that said Letters Patent is hereby corrected as shown below:

On the Title Page, after Item (60), "Related U.S. Application Data," and before Item (51), "Int. Cl.," insert the following missing data:

--(30)  Foreign Application Priority Data
 January 7, 2004  (FR)  04 50041--.

In claim 13, column 38, line 44, "alkylsuiphonyl" should read --alkylsulphonyl;--.

In claim 13, column 38, line 50, "groups," should read --group,--.

In claim 22, column 40, line 17, "according claim" should read --according to claim--.

Signed and Sealed this

Twenty-ninth Day of April, 2008

JON W. DUDAS
*Director of the United States Patent and Trademark Office*